(12) United States Patent
Chow et al.

(10) Patent No.: US 9,095,546 B2
(45) Date of Patent: Aug. 4, 2015

(54) HUMAN RESPIRATORY SYNCYTIAL VIRUS (RSV) VACCINE

(75) Inventors: Yen-Hung Chow, Zhunan Town (TW); Hsiao-Yun Shao, Zhunan Town (TW); Charles Sia, Zhunan Town (TW); Pele Chong, Zhunan Town (TW)

(73) Assignee: National Health Research Institutes, Miaoli County (TW)

( * ) Notice: Subject to any disclaimer, the term of this patent is extended or adjusted under 35 U.S.C. 154(b) by 1151 days.

(21) Appl. No.: 12/505,998

(22) Filed: Jul. 20, 2009

(65) Prior Publication Data

US 2011/0014220 A1    Jan. 20, 2011

(51) Int. Cl.
*A61K 39/155* (2006.01)
*A61K 39/12* (2006.01)
*A61K 39/00* (2006.01)

(52) U.S. Cl.
CPC ....... *A61K 39/155* (2013.01); *A61K 2039/5252* (2013.01); *A61K 2039/5256* (2013.01); *A61K 2039/543* (2013.01); *A61K 2039/545* (2013.01); *A61K 2039/57* (2013.01); *C12N 2710/10343* (2013.01); *C12N 2760/18534* (2013.01)

(58) Field of Classification Search
None
See application file for complete search history.

(56) References Cited

PUBLICATIONS

Connors et al. 1992 Vaccine vol. 10, pp. 475-484.*
Hsu et al., J Infect Dis. Oct. 1992;166(4):769-75.*
Printout titled—fusion protein [Human respiratory syncytial virus]—Protein—NCBI, printed Nov. 25, 2011 Genbank ABA18346.1, Aug. 25, 2006.*

* cited by examiner

*Primary Examiner* — Mary E Mosher
*Assistant Examiner* — Myron Hill
(74) *Attorney, Agent, or Firm* — Cesari and McKenna, LLP

(57) ABSTRACT

The present invention relates to a vaccine composition against the infection of human respiratory syncytial virus (RSV) comprising a replication-defective recombinant adenovirus carrying a nucleotide sequence encoding the F protein of RSV or fragment thereof. A method of preventing RSV infection-related diseases using the vaccine composition of the present invention is also provided.

16 Claims, 13 Drawing Sheets

SEQUENCE LISTING

```
<160> NUMBER OF SEQ ID NOS: 8

<210> SEQ ID NO 1
<211> LENGTH: 1722
<212> TYPE: DNA
<213> ORGANISM: respiratory syncytial virus
```

```
<220> FEATURE:
<221> NAME/KEY: CDS
<222> LOCATION: (1)..(1722)
<300> PUBLICATION INFORMATION:
<308> DATABASE ACCESSION NUMBER: GenBank / NC_001803
<309> DATABASE ENTRY DATE: 2008-12-08
<313> RELEVANT RESIDUES IN SEQ ID NO: (1)..(1722)

<400> SEQUENCE: 1 atg gag ctg ccc atc ctg aag gct aac gct atc acc acc atc ctg gct        48
Met Glu Leu Pro Ile Leu Lys Ala Asn Ala Ile Thr Thr Ile Leu Ala
1               5                   10                  15 gct gtg acc ctg tgc ttc gct tcc tcc cag aac atc acc gag gag ttc        96
Ala Val Thr Leu Cys Phe Ala Ser Ser Gln Asn Ile Thr Glu Glu Phe
            20                  25                  30 tac cag tcc acc tgc tcc gct gtg tcc aag ggt tac ctg tcc gct ctg       144
Tyr Gln Ser Thr Cys Ser Ala Val Ser Lys Gly Tyr Leu Ser Ala Leu
        35                  40                  45 cgt acc ggt tgg tac acc tcc gtg atc acc atc gag ctg tcc aac atc       192
Arg Thr Gly Trp Tyr Thr Ser Val Ile Thr Ile Glu Leu Ser Asn Ile
    50                  55                  60 aag gag aac aag tgc aac ggt acc gac gct aag gtg aag ctg atc aag       240
Lys Glu Asn Lys Cys Asn Gly Thr Asp Ala Lys Val Lys Leu Ile Lys
65                  70                  75                  80 cag gag ctg gac aag tac aag aac gct gtg acc gag ctg cag ctg ctg       288
Gln Glu Leu Asp Lys Tyr Lys Asn Ala Val Thr Glu Leu Gln Leu Leu
                85                  90                  95 atg cag tcc acc ccc gct gct aac aac cgt gct cgt cgt gag ctg ccc       336
Met Gln Ser Thr Pro Ala Ala Asn Asn Arg Ala Arg Arg Glu Leu Pro
            100                 105                 110 cgt ttc atg aac tac acc ctg aac aac acc aag aac acc aac gtg acc       384
Arg Phe Met Asn Tyr Thr Leu Asn Asn Thr Lys Asn Thr Asn Val Thr
        115                 120                 125 ctg tcc aag aag cgt aag cgt cgt ttc ctg ggt ttc ctg ctg ggt gtg       432
Leu Ser Lys Lys Arg Lys Arg Arg Phe Leu Gly Phe Leu Leu Gly Val
    130                 135                 140 ggt tcc gct atc gct tcc ggt atc gct gtg tcc aag gtg ctg cac ctg       480
Gly Ser Ala Ile Ala Ser Gly Ile Ala Val Ser Lys Val Leu His Leu
145                 150                 155                 160 gag ggt gag gtg aac aag atc aag tcc gct ctg ctg tcc acc aac aag       528
Glu Gly Glu Val Asn Lys Ile Lys Ser Ala Leu Leu Ser Thr Asn Lys
                165                 170                 175 gct gtg gtg tcc ctg tcc aac ggt gtg tcc gtg ctg acc tcc aag gtg       576
Ala Val Val Ser Leu Ser Asn Gly Val Ser Val Leu Thr Ser Lys Val
            180                 185                 190 ctg gac ctg aag aac tac atc gac aag cag ctg ctg ccc atc gtg aac       624
Leu Asp Leu Lys Asn Tyr Ile Asp Lys Gln Leu Leu Pro Ile Val Asn
        195                 200                 205 aag cag tcc tgc cgt atc tcc aac atc gag acc gtg atc gag ttc cag       672
Lys Gln Ser Cys Arg Ile Ser Asn Ile Glu Thr Val Ile Glu Phe Gln
    210                 215                 220 cag aag aac aac cgt ctg ctg gag atc acc cgt gag ttc tcc gtg aac       720
Gln Lys Asn Asn Arg Leu Leu Glu Ile Thr Arg Glu Phe Ser Val Asn
225                 230                 235                 240 gct ggt gtg acc acc ccc gtg tcc acc tac atg ctg acc aac tcc gag       768
Ala Gly Val Thr Thr Pro Val Ser Thr Tyr Met Leu Thr Asn Ser Glu
                245                 250                 255 ctg ctg tcc ctg atc aac gac atg ccc atc acc aac gac cag aag aag       816
Leu Leu Ser Leu Ile Asn Asp Met Pro Ile Thr Asn Asp Gln Lys Lys
            260                 265                 270
```

```
ctg atg tcc aac aac gtg cag atc gtg cgt cag cag tcc tac tcc atc    864
Leu Met Ser Asn Asn Val Gln Ile Val Arg Gln Gln Ser Tyr Ser Ile
    275                 280                 285 atg tcc atc atc aag gag gag gtg ctg gct tac gtg gtg cag ctg ccc    912
Met Ser Ile Ile Lys Glu Glu Val Leu Ala Tyr Val Val Gln Leu Pro
290                 295                 300 ctg tac ggt gtg atc gac acc ccc tgc tgg aag ctg cac acc tcc ccc    960
Leu Tyr Gly Val Ile Asp Thr Pro Cys Trp Lys Leu His Thr Ser Pro
305                 310                 315                 320 ctg tgc acc acc aac acc aag gag ggt tcc aac atc tgc ctg acc cgt   1008
Leu Cys Thr Thr Asn Thr Lys Glu Gly Ser Asn Ile Cys Leu Thr Arg
                325                 330                 335 acc gac cgt ggt tgg tac tgc gac aac gct ggt tcc gtg tcc ttc ttc   1056
Thr Asp Arg Gly Trp Tyr Cys Asp Asn Ala Gly Ser Val Ser Phe Phe
            340                 345                 350 ccc cag gct gag acc tgc aag gtg cag tcc aac cgt gtg ttc tgc gac   1104
Pro Gln Ala Glu Thr Cys Lys Val Gln Ser Asn Arg Val Phe Cys Asp
                355                 360                 365 acc atg aac tcc ctg acc ctg ccc tcc gag gtg aac ctg tgc aac gtg   1152
Thr Met Asn Ser Leu Thr Leu Pro Ser Glu Val Asn Leu Cys Asn Val
    370                 375                 380 gac atc ttc aac ccc aag tac gac tgc aag atc atg acc tcc aag acc   1200
Asp Ile Phe Asn Pro Lys Tyr Asp Cys Lys Ile Met Thr Ser Lys Thr
385                 390                 395                 400 gac gtg tcc tcc tcc gtg atc acc tcc ctg ggt gct atc gtg tcc tgc   1248
Asp Val Ser Ser Ser Val Ile Thr Ser Leu Gly Ala Ile Val Ser Cys
                405                 410                 415 tac ggt aag acc aag tgc acc gct tcc aac aag aac cgt ggt atc atc   1296
Tyr Gly Lys Thr Lys Cys Thr Ala Ser Asn Lys Asn Arg Gly Ile Ile
            420                 425                 430 aag acc ttc tcc aac ggt tgc gac tac gtg tcc aac aag ggt gtg gac   1344
Lys Thr Phe Ser Asn Gly Cys Asp Tyr Val Ser Asn Lys Gly Val Asp
                435                 440                 445 acc gtg tcc gtg ggt aac acc ctg tac tac gtg aac aag cag gag ggt   1392
Thr Val Ser Val Gly Asn Thr Leu Tyr Tyr Val Asn Lys Gln Glu Gly
    450                 455                 460 aag tcc ctg tac gtg aag ggt gag ccc atc atc aac ttc tac gac ccc   1440
Lys Ser Leu Tyr Val Lys Gly Glu Pro Ile Ile Asn Phe Tyr Asp Pro
465                 470                 475                 480 ctg gtg ttc ccc tcc gac gag ttc gac gct tcc atc tcc cag gtg aac   1488
Leu Val Phe Pro Ser Asp Glu Phe Asp Ala Ser Ile Ser Gln Val Asn
                485                 490                 495 gag aag atc aac cag tcc ctg gct ttc atc cgt aag tcc gac gag ctg   1536
Glu Lys Ile Asn Gln Ser Leu Ala Phe Ile Arg Lys Ser Asp Glu Leu
            500                 505                 510 ctg cac aac gtg aac gct ggt aag tcc acc acc aac atc atg atc acc   1584
Leu His Asn Val Asn Ala Gly Lys Ser Thr Thr Asn Ile Met Ile Thr
                515                 520                 525 acc atc atc atc gtg atc atc gtg atc ctg ctg tcc ctg atc gct gtg   1632
Thr Ile Ile Ile Val Ile Ile Val Ile Leu Leu Ser Leu Ile Ala Val
    530                 535                 540 ggt ctg ctg ctg tac tgc aag gct cgt tcc acc ccc gtg acc ctg tcc   1680
Gly Leu Leu Leu Tyr Cys Lys Ala Arg Ser Thr Pro Val Thr Leu Ser
545                 550                 555                 560 aag gac cag ctg tcc ggt atc aac aac atc gct ttc tcc aac             1722
Lys Asp Gln Leu Ser Gly Ile Asn Asn Ile Ala Phe Ser Asn
                565                 570
```

```
<210> SEQ ID NO 2
<211> LENGTH: 574
<212> TYPE: PRT
<213> ORGANISM: respiratory syncytial virus

<400> SEQUENCE: 2

Met Glu Leu Pro Ile Leu Lys Ala Asn Ala Ile Thr Thr Ile Leu Ala
 1               5                  10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380
```

```
Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 3
<211> LENGTH: 1572
<212> TYPE: DNA
<213> ORGANISM: respiratory syncytial virus
<220> FEATURE:
<221> NAME/KEY: CDS
<222> LOCATION: (1)..(1572)
<300> PUBLICATION INFORMATION:
<308> DATABASE ACCESSION NUMBER: GenBank / NC_001803
<309> DATABASE ENTRY DATE: 2008-12-08
<313> RELEVANT RESIDUES IN SEQ ID NO: (1)..(1572)

<400> SEQUENCE: 3 atg gag ctg ccc atc ctg aag gct aac gct atc acc acc atc ctg gct      48
Met Glu Leu Pro Ile Leu Lys Ala Asn Ala Ile Thr Thr Ile Leu Ala
1               5                   10                  15 gct gtg acc ctg tgc ttc gct tcc tcc cag aac atc acc gag gag ttc      96
Ala Val Thr Leu Cys Phe Ala Ser Ser Gln Asn Ile Thr Glu Glu Phe
            20                  25                  30 tac cag tcc acc tgc tcc gct gtg tcc aag ggt tac ctg tcc gct ctg     144
Tyr Gln Ser Thr Cys Ser Ala Val Ser Lys Gly Tyr Leu Ser Ala Leu
        35                  40                  45 cgt acc ggt tgg tac acc tcc gtg atc acc atc gag ctg tcc aac atc     192
Arg Thr Gly Trp Tyr Thr Ser Val Ile Thr Ile Glu Leu Ser Asn Ile
    50                  55                  60 aag gag aac aag tgc aac ggt acc gac gct aag gtg aag ctg atc aag     240
Lys Glu Asn Lys Cys Asn Gly Thr Asp Ala Lys Val Lys Leu Ile Lys
65                  70                  75                  80 cag gag ctg gac aag tac aag aac gct gtg acc gag ctg cag ctg ctg     288
Gln Glu Leu Asp Lys Tyr Lys Asn Ala Val Thr Glu Leu Gln Leu Leu
                85                  90                  95 atg cag tcc acc ccc gct gct aac aac cgt gct cgt cgt gag ctg ccc     336
Met Gln Ser Thr Pro Ala Ala Asn Asn Arg Ala Arg Arg Glu Leu Pro
            100                 105                 110
```

-continued

| | | |
|---|---|---|
| cgt ttc atg aac tac acc ctg aac aac acc aag aac acc aac gtg acc<br>Arg Phe Met Asn Tyr Thr Leu Asn Asn Thr Lys Asn Thr Asn Val Thr<br>115                        120                       125 | 384 |
| ctg tcc aag aag cgt aag cgt cgt ttc ctg ggt ttc ctg ctg ggt gtg<br>Leu Ser Lys Lys Arg Lys Arg Arg Phe Leu Gly Phe Leu Leu Gly Val<br>    130                     135                     140 | 432 |
| ggt tcc gct atc gct tcc ggt atc gct gtg tcc aag gtg ctg cac ctg<br>Gly Ser Ala Ile Ala Ser Gly Ile Ala Val Ser Lys Val Leu His Leu<br>145                       150                       155                   160 | 480 |
| gag ggt gag gtg aac aag atc aag tcc gct ctg ctg tcc acc aac aag<br>Glu Gly Glu Val Asn Lys Ile Lys Ser Ala Leu Leu Ser Thr Asn Lys<br>             165                     170                     175 | 528 |
| gct gtg gtg tcc ctg tcc aac ggt gtg tcc gtg ctg acc tcc aag gtg<br>Ala Val Val Ser Leu Ser Asn Gly Val Ser Val Leu Thr Ser Lys Val<br>        180                     185                     190 | 576 |
| ctg gac ctg aag aac tac atc gac aag cag ctg ctg ccc atc gtg aac<br>Leu Asp Leu Lys Asn Tyr Ile Asp Lys Gln Leu Leu Pro Ile Val Asn<br>195                       200                      205 | 624 |
| aag cag tcc tgc cgt atc tcc aac atc gag acc gtg atc gag ttc cag<br>Lys Gln Ser Cys Arg Ile Ser Asn Ile Glu Thr Val Ile Glu Phe Gln<br>    210                     215                     220 | 672 |
| cag aag aac aac cgt ctg ctg gag atc acc cgt gag ttc tcc gtg aac<br>Gln Lys Asn Asn Arg Leu Leu Glu Ile Thr Arg Glu Phe Ser Val Asn<br>225                       230                      235                   240 | 720 |
| gct ggt gtg acc acc ccc gtg tcc acc tac atg ctg acc aac tcc gag<br>Ala Gly Val Thr Thr Pro Val Ser Thr Tyr Met Leu Thr Asn Ser Glu<br>             245                     250                     255 | 768 |
| ctg ctg tcc ctg atc aac gac atg ccc atc acc aac gac cag aag aag<br>Leu Leu Ser Leu Ile Asn Asp Met Pro Ile Thr Asn Asp Gln Lys Lys<br>        260                     265                     270 | 816 |
| ctg atg tcc aac aac gtg cag atc gtg cgt cag cag tcc tac tcc atc<br>Leu Met Ser Asn Asn Val Gln Ile Val Arg Gln Gln Ser Tyr Ser Ile<br>275                       280                     285 | 864 |
| atg tcc atc atc aag gag gag gtg ctg gct tac gtg gtg cag ctg ccc<br>Met Ser Ile Ile Lys Glu Glu Val Leu Ala Tyr Val Val Gln Leu Pro<br>    290                     295                     300 | 912 |
| ctg tac ggt gtg atc gac acc ccc tgc tgg aag ctg cac acc tcc ccc<br>Leu Tyr Gly Val Ile Asp Thr Pro Cys Trp Lys Leu His Thr Ser Pro<br>305                       310                      315                  320 | 960 |
| ctg tgc acc acc aac acc aag gag ggt tcc aac atc tgc ctg acc cgt<br>Leu Cys Thr Thr Asn Thr Lys Glu Gly Ser Asn Ile Cys Leu Thr Arg<br>             325                     330                     335 | 1008 |
| acc gac cgt ggt tgg tac tgc gac aac gct ggt tcc gtg tcc ttc ttc<br>Thr Asp Arg Gly Trp Tyr Cys Asp Asn Ala Gly Ser Val Ser Phe Phe<br>        340                     345                     350 | 1056 |
| ccc cag gct gag acc tgc aag gtg cag tcc aac cgt gtg ttc tgc gac<br>Pro Gln Ala Glu Thr Cys Lys Val Gln Ser Asn Arg Val Phe Cys Asp<br>             355                     360                     365 | 1104 |
| acc atg aac tcc ctg acc ctg ccc tcc gag gtg aac ctg tgc aac gtg<br>Thr Met Asn Ser Leu Thr Leu Pro Ser Glu Val Asn Leu Cys Asn Val<br>    370                     375                     380 | 1152 |
| gac atc ttc aac ccc aag tac gac tgc aag atc atg acc tcc aag acc<br>Asp Ile Phe Asn Pro Lys Tyr Asp Cys Lys Ile Met Thr Ser Lys Thr<br>385                       390                     395                   400 | 1200 |
| gac gtg tcc tcc tcc gtg atc acc tcc ctg ggt gct atc gtg tcc tgc<br>Asp Val Ser Ser Ser Val Ile Thr Ser Leu Gly Ala Ile Val Ser Cys<br>        405                     410                     415 | 1248 |
| tac ggt aag acc aag tgc acc gct tcc aac aag aac cgt ggt atc atc<br>Tyr Gly Lys Thr Lys Cys Thr Ala Ser Asn Lys Asn Arg Gly Ile Ile<br>             420                     425                     430 | 1296 |

```
aag acc ttc tcc aac ggt tgc gac tac gtg tcc aac aag ggt gtg gac       1344
Lys Thr Phe Ser Asn Gly Cys Asp Tyr Val Ser Asn Lys Gly Val Asp
        435                 440                 445 acc gtg tcc gtg ggt aac acc ctg tac tac gtg aac aag cag gag ggt       1392
Thr Val Ser Val Gly Asn Thr Leu Tyr Tyr Val Asn Lys Gln Glu Gly
    450                 455                 460 aag tcc ctg tac gtg aag ggt gag ccc atc atc aac ttc tac gac ccc       1440
Lys Ser Leu Tyr Val Lys Gly Glu Pro Ile Ile Asn Phe Tyr Asp Pro
465                 470                 475                 480 ctg gtg ttc ccc tcc gac gag ttc gac gct tcc atc tcc cag gtg aac       1488
Leu Val Phe Pro Ser Asp Glu Phe Asp Ala Ser Ile Ser Gln Val Asn
                485                 490                 495 gag aag atc aac cag tcc ctg gct ttc atc cgt aag tcc gac gag ctg       1536
Glu Lys Ile Asn Gln Ser Leu Ala Phe Ile Arg Lys Ser Asp Glu Leu
            500                 505                 510 ctg cac aac gtg aac gct ggt aag tcc acc acc aac                       1572
Leu His Asn Val Asn Ala Gly Lys Ser Thr Thr Asn
                515                 520
```

<210> SEQ ID NO 4
<211> LENGTH: 524
<212> TYPE: PRT
<213> ORGANISM: respiratory syncytial virus

<400> SEQUENCE: 4

```
Met Glu Leu Pro Ile Leu Lys Ala Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn
        515                 520

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
acatcgacaa gcagctgctg c                                          21

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
gaggtgaacc tgtgcaacg                                             19
```

```
<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
atcctgaagg ctaaggctat c                                              21

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
accaacgtga ccctgtccaa                                                20
```

HUMAN RESPIRATORY SYNCYTIAL VIRUS (RSV) VACCINE

FIELD OF THE INVENTION

The preset invention relates to a human respiratory syncytial virus (RSV) vaccine; in particular, a vaccine composition comprising a recombinant adenoviral construct carrying the nucleotide encoding a RSV protein.

BACKGROUND OF THE INVENTION

Respiratory syncytial virus (RSV) is a single-stranded, negative sense RNA pleomorphic enveloped Pneumovirus of the Paramyxoviruidae family. Human RSV genome contains eight structural genes and two non-structural genes, wherein the major genes code for the attachment glycoprotein (G protein), the fusion protein (F protein), and a small hydrophobic envelope protein (SH protein), respectively.

The infection of RSV would lead to the induction of both humoral and cellular immune responses directed against the virus. It was proved in several studies in animal models that the RSV-specific neutralizing antibodies and cytotoxic lymphocytes (CTLs) contributed to a protection against RSV infection and/or diseases. For example, it was reported that RSV-specific antibodies played an important role in prevention from the RSV infection in terms of the protective efficacy of the passive transfer of immune sera containing RSV-specific antibodies of unvaccinated mice challenged by a live RSV (Graham et al., Immunoprophylaxis and immunotherapy of respiratory syncytial virus-infected mice with respiratory syncytial virus-specific immune serum; Pediatr Res 1993 August; 34(2):167-72). It was also reported that RSV-specific CTLs were detected more readily in adults who developed mild symptoms due to RSV infection exposure (Isaacs D., Viral subunit vaccines; Lancet 1991 May 18; 337 (8751): 1223-4).

It was evidenced that F protein of RSV as target of vaccine antigen was better than G protein of RSV because the recombinant vaccinia virus expressing the G protein of RSV (vacvG) enhanced pulmonary eosinophilia upon RSV infection of mice (as reported in, for example, Openshaw et al., Pulmonary eosinophilic response to respiratory syncytial virus infection in mice sensitized to the major surface glycoprotein G; Int Immunol 1992 April; 4(4):493-500). However, it was also reported that Th-2 type response to RSV infection after F1-RSV-vaccination (a vaccination with the F1 subunit of F protein of RSV) played a role in an abnormal response, characterized by extensive eosinophils increasing in the blood, wheezing, and hyper reactive airways (Kim et al., Respiratory syncytial virus disease in infants despite prior administration of antigenic inactivated vaccine; Am J Epidemiol 1969 April; 89(4):422-34), and that the Th2-associated cytokines IL-4 and IL-13 both promoted the development of pulmonary eosinophilia (Johnson and Graham, Secreted respiratory syncytial virus G glycoprotein induces interleukin-5 (IL-5), IL-13, and eosinophilia by an IL-4-independent mechanism; J Virol 1999 October; 73(10):8485-95; and Johnson et al., IL-13 is sufficient for respiratory syncytial virus G glycoprotein-induced eosinophilia after respiratory syncytial virus challenge; J Immunol 2003 Feb. 15; 170(4): 2037-45).

Given the above, it is still desired to develop a new vaccine for prevention against the RSV infection or the vaccine-enhanced diseases without undesired side effects, such as eosinophilia.

BRIEF SUMMARY OF THE INVENTION

The present invention features a novel RSV DNA vaccine characterized by a replication-defective recombinant adenoviral construct carrying a nucleotide sequence encoding F protein of RSV. It is unexpectedly discovered that the RSV vaccine of the present invention does not have undesired side effects, such as inflammation and eosinophila, present in the RSV vaccines known in the art.

In one aspect, the invention is to provide a vaccine composition comprising a replication-defective recombinant adenoviral construct carrying a nucleotide sequence encoding a polypeptide of F protein of RSV or fragments thereof.

In the other aspect, the invention is to provide a method of preventing RSV infection-related diseases comprising administering to a subject in need thereof a vaccine composition comprising a replication-defective recombinant adenoviral construct carrying a nucleotide sequence encoding a polypeptide of F protein of RSV or fragments thereof.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the preferred embodiments shown.

In the drawings:

Figure 1C:
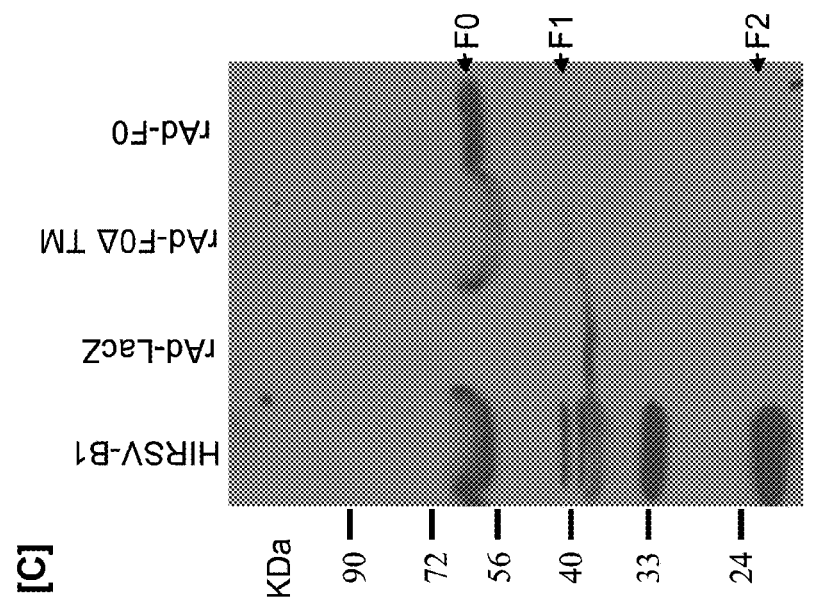

FIG. 1C is an image showing the immunoblotting of the lysates prepared from the constructs rAd-F0- and rAd-F0ΔTM-infected 293A cells; wherein the F0 and F0ΔTM proteins had molecular sizes of 62 KDa and 57 KDa, respectively.

FIG. 2 shows the titles of the RSV F-specific IgA antibodies in immune sera and bronchoalveolar lavage (BALs) of the four groups of mice vaccinated with rAd-F0, rAd-F0ΔTM, rAd-LacZ, and HIRSV, respectively.

Figure 8:
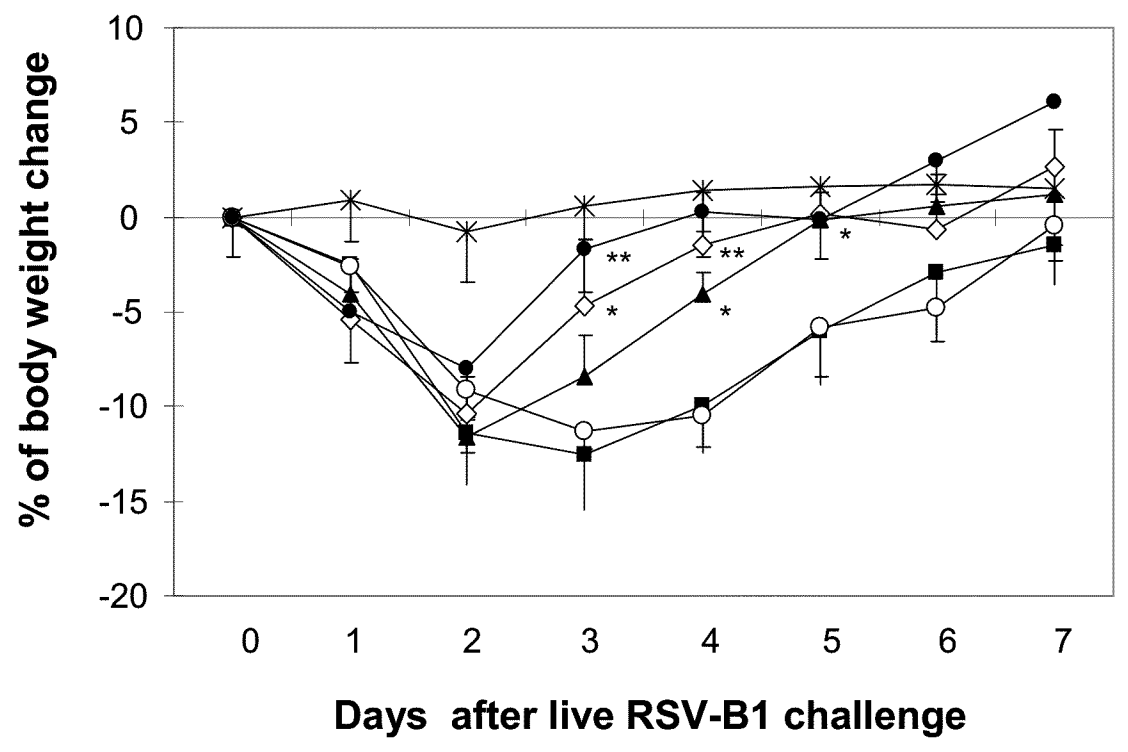

FIG. 8 shows the monitoring of body weight of experimental mice post live RSV-B1 challenge, including the four groups of mice immunized twice via the intranasal route with PBS (■), rAd-lacZ (○), rAd-F0 (•), rAd-F0ΔTM (Δ), HIRSV-B1 (▲), respectively, as well as an untreated group (*); wherein the results were expressed as % (mean) with one standard deviation of body weight change for 5 mice in each group (* and ** represented p<0.05 and p<0.01, respectively, and it was indicated that the results of the groups with rAd-F0 and rAd-F0ΔTM were significant difference from the rAd-LacZ-immunized control).

DETAILED DESCRIPTION OF THE INVENTION

Figure 1A:
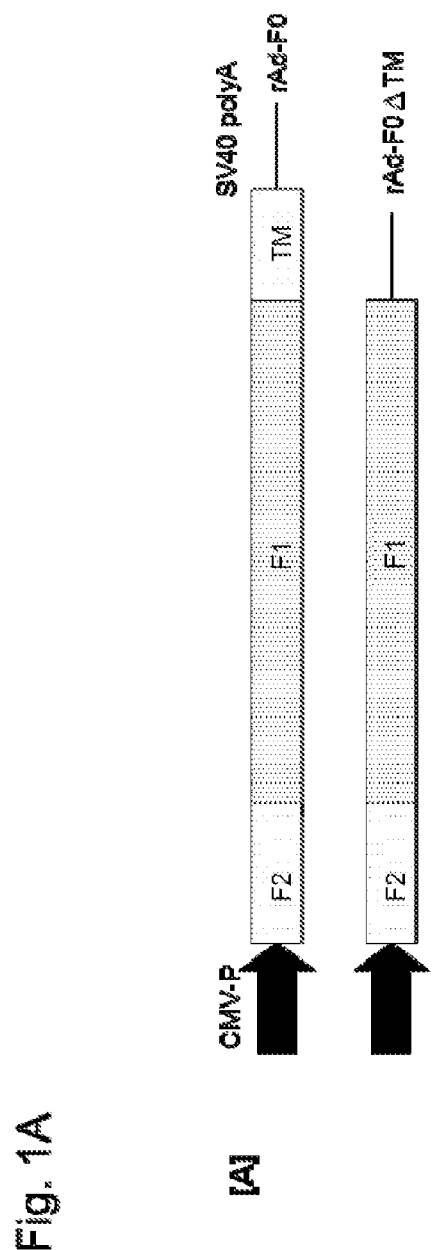
FIG. 1A shows the schematic maps of the parts of the two recombinant adenoviral constructs of the present invention, rAd-F0 and rAd-F0ΔTM, wherein the construct rAd-F0 is the full-length of F gene of RSV-B1 (F0) cloned into the replication defective adenovirus construct, and the construct rAd-F0ΔTM is the transmembrane coding region-truncated F gene of of RSV-B1 (F0ΔTM) cloned into the replication defective adenovirus construct.
Figure 1B:
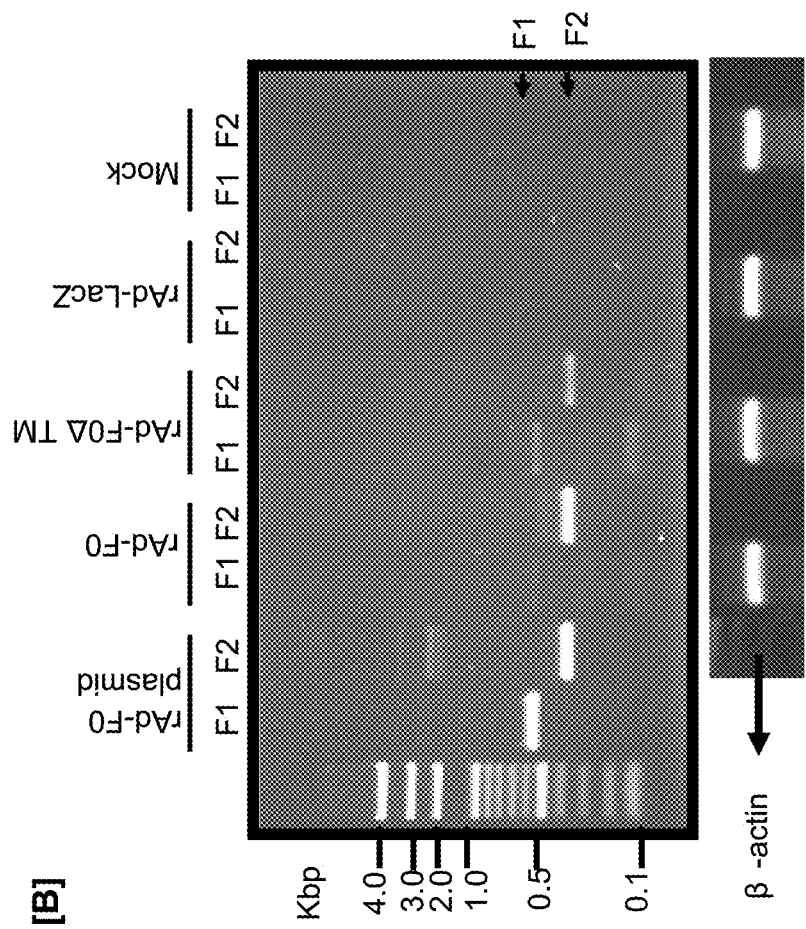
FIG. 1B is an image showing the expression of the F0 and F0ΔTM genes in the 293A cells; wherein the PCR products of 559 bps for F0, 378 bps for F0ΔTM, and 267 bps for β-actin were found.
Figure 3A:
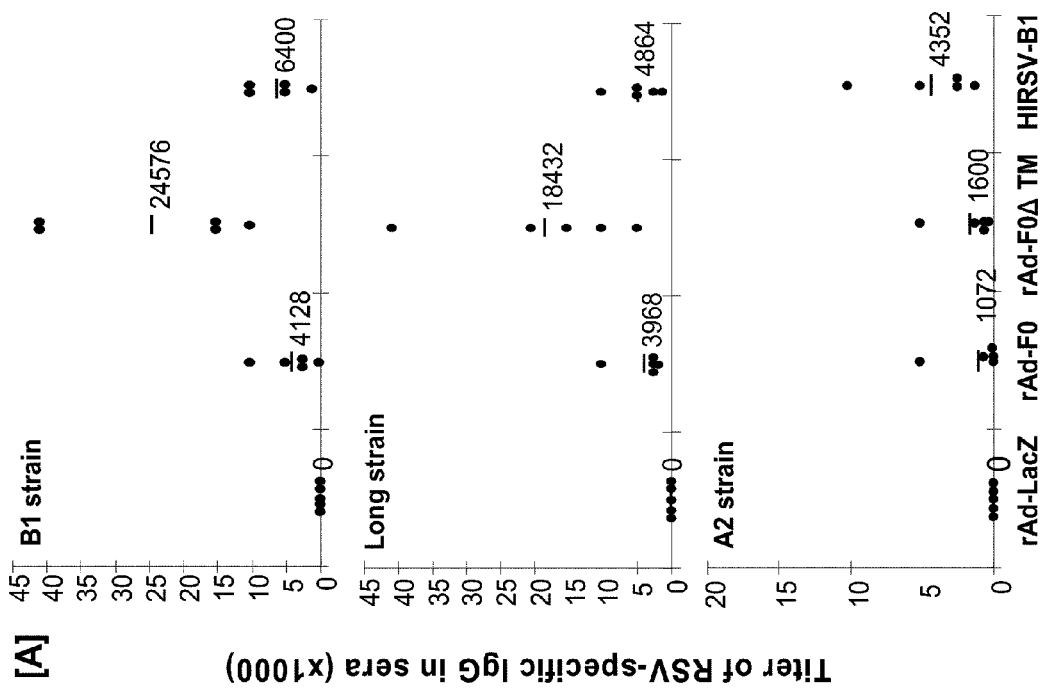
FIG. 3A shows the titles of RSV-specific IgG of the BABL/c mice's sera wherein each of the bars corresponded to the mean title for each of the groups with rAd-F0, rAd-F0ΔTM, rAd-LacZ, and HIRSV-B1, respectively.
Figure 3B:
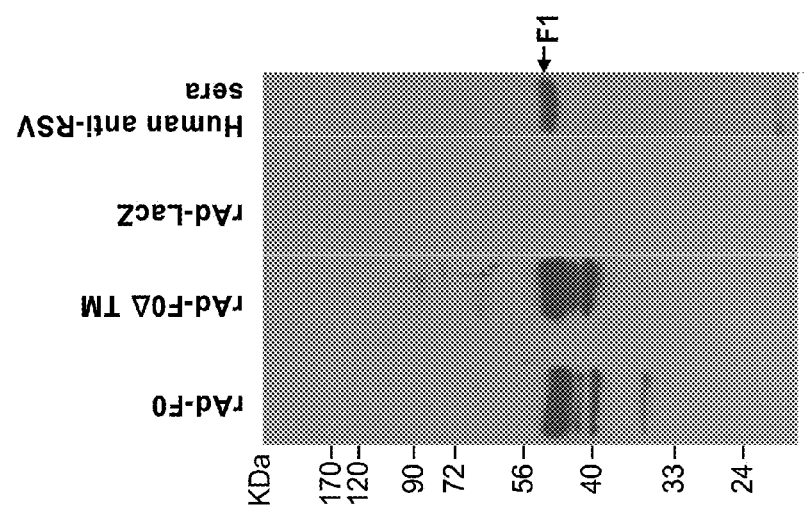
FIG. 3B is an image showing the immunoblotting of the SDS-PAGE electrophoresis/membrane transfer of the heat-inactivated RSV-B1 at the amount of $10^2$ particles as antigen immunoblotted with the collected pooled-sera of each group (1:500 dilution) or human polyclonal anti-RSV F sera (1:200 dilution).
Figure 4A:
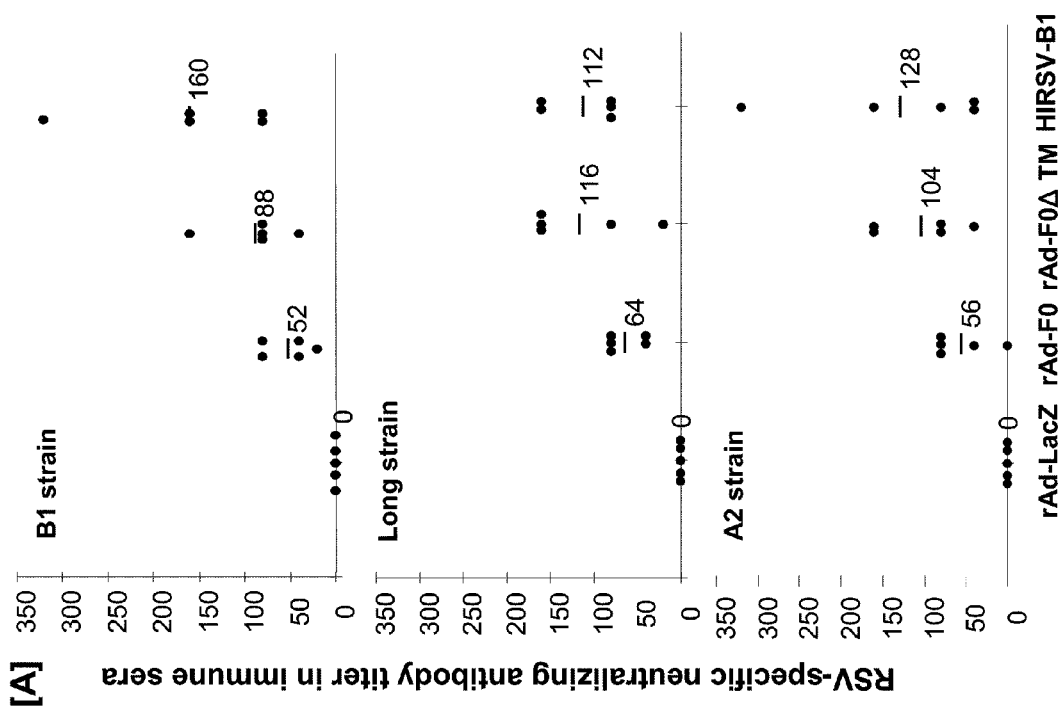
FIG. 4A shows the activity of the individual immune sera at varying dilutions; wherein the results were expressed as neutralizing titers in terms of the dilutions of immune sera giving 60% inhibition of plaque-formation.
Figure 4B:
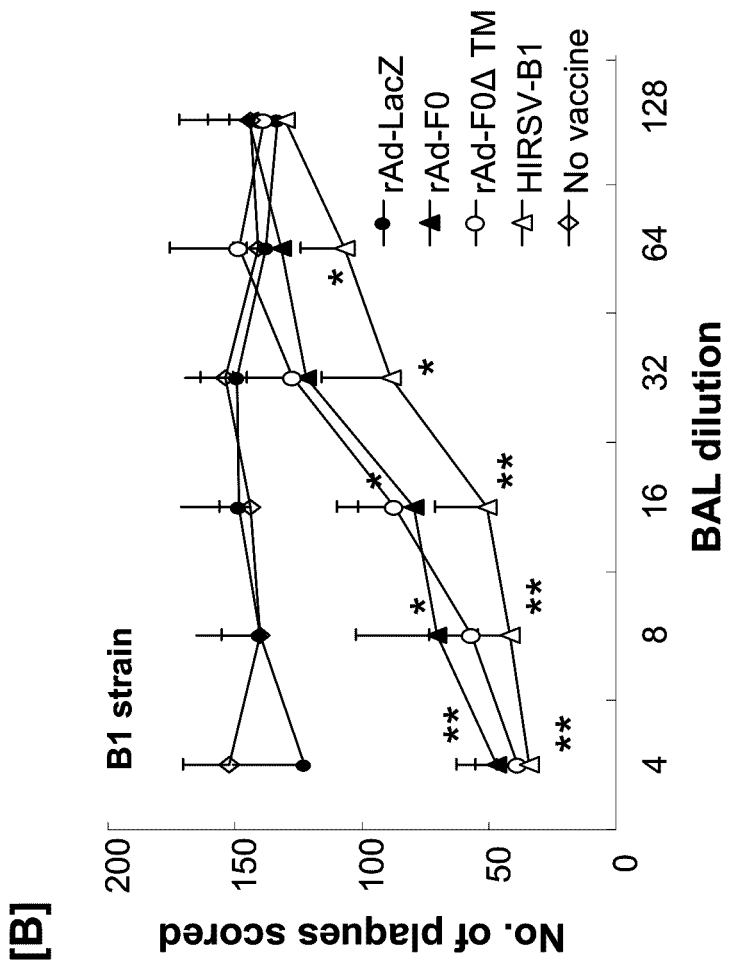
FIG. 4B shows the numbers of plaques of the BALs at varying dilutions, 4×, 8×, 16×, 32×, 64× and 128×, respectively, as scored after 4 days of culture; wherein * and ** represented p<0.05 and p<0.01, respectively, and the results indicated that the activity of the groups rAd-F0 and rAd-F0ΔTM were significantly better than that of the rAd-LacZ-immunized control (the group of rAd-LacZ).

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant" is used to describe a polynucleotide or nucleic acid having sequences that are not naturally joined together. A recombinant nucleic acid may be present in the form of a construct. The term "construct" as used herein may contain a given nucleotide sequence of interest, and some sequence required for expression of the nucleotide sequence of interest, such as a regulatory sequence. Constructs may be used for expressing the given nucleotide sequence or maintaining the given nucleotide sequence for replicating it, manipulating it or transferring it between different locations (e.g., between different organisms). Constructs can be introduced into a suitable host cell for the above mentioned purposes.

Examples of constructs include, but are not limited to, plasmids, cosmids, phages, YACs or PACs. Typically, in a construct, the given nucleotide sequence is operatively linked to the regulatory sequence such that when the constructs are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g.,—mating factor signal) and other control sequence (e.g., Shine-Dalgano sequences and termination sequences). Preferably, constructs may further contain a marker sequence (e.g., an antibiotic resistant marker sequence) for the subsequent screening procedure. More preferably, in constructs, the given nucleotide sequence of interest may be connected to another nucleotide sequence other than the above-mentioned regulatory sequence such that a fused polypeptide is produced and beneficial to the subsequent purification procedure. Said fused polypeptide includes, but is not limited to, a His-tag fused polypeptide and a GST fused polypeptide.

The term "fragment" as used herein refers to a peptide that has an amino-terminal and/or carboxy-terminal deletion, but where the remaining amino acid sequence is identical to the corresponding positions in the sequence of a major or target polypeptide or protein, for example, from a full-length sequence of a protein.

The term "vaccine" refers to an agent or composition containing an active component effective to induce a therapeutic degree of immunity in a subject against a certain pathogen or disease. Traditionally, the active component of a vaccine is a polypeptide derived from a pathogen which is the target of the vaccine. The term "DNA vaccine" refers to a vaccine wherein the active component is DNAs.

A "subject" in need of therapy is a human or non-human mammal. Non-human mammals include, but are not limited to, primates, ungulates, canines and felines.

The term "adenovirus" as referred to herein indicates over 47 adenoviral subtypes isolated from humans, and as many from other mammals and birds. See, Strauss, "Adenovirus infections in humans," in The Adenoviruses, Ginsberg, ed., Plenum Press, New York, N.Y., pp. 451 596 (1984).

The present invention provides a vaccine composition comprising a replication-defective recombinant adenoviral construct carrying a nucleotide sequence encoding a polypeptide of F protein of RSV or fragment thereof.

In one example of the invention, the vaccine composition comprises a replication-defective recombinant adenoviral construct transformed with a nucleotide sequence encoding F protein of RSV. As demonstrated in the examples below, the vaccine composition of the present invention effectively elicited both humoral and cellular immune responses. The vaccine composition of the present invention is further characterized in that it does not have undesired side effects, such as eosinophilia and inflammatory responses associated with interleukins, such as IL-17.

According to the invention, the F protein of RSV may be derived from any strains of naturally-occurring or recombinant RSV, preferably from human RSV strains, such as A2, long, or B strains. In one example of the invention, the RSV strain is RSV-B1 strain.

According to the invention, the F protein of RSV may be the full length of F protein of RSV or fragment thereof. In one embodiment of the invention, the nucleotide sequence encoding F protein of RSV encodes the full length of F protein of RSV (F0), such as the amino acid of SEQ ID NO: 2. In one example of the invention, the nucleotide sequence encoding F protein of RSV has the nucleotide sequence of SEQ ID NO: 1. The F protein of RSV may be any sequence that is at least about 75%, preferably more than about 85%, homologous to the nucleotide sequence of SEQ ID NO: 1.

In another embodiment of the invention, the nucleotide sequence may alternatively encode a fragment of F protein of RSV. The fragment may be resulted from either or both of amino-terminal and carboxy-terminal deletions. The extent of deletion may be determined by a person skilled in the art to, for example, achieve better yield of the recombinant adenovirus. In one example of the present invention, the fragment was the transmembrane coding region-truncated F protein of RSV (F0ΔTM), which was deleted from the full-length sequence of F protein. In one Embodiment of the invention, the nucleotide sequence is the transmembrane coding region-truncated F protein of RSV (F0ΔTM), such as the amino acid sequence of SEQ ID NO: 3. In one example of the invention, the transmembrane coding region-truncated F protein of RSV (F0ΔTM) has the nucleotide sequence of SEQ ID NO: 3. The fragments of F protein may also be F1 domain or F2 domain of F protein.

The adenoviral construct which serves as the backbone of the recombinant vaccine construct of the present invention is preferably a "first generation" adenoviral construct. This type of adenoviral constructs is known in the art, and is characterized by being replication-defective. These viruses typically have a deleted or inactivated E1 gene region, and preferably additionally have a deleted or inactivated E3 gene region. In one embodiment of the present invention, the first generation replication-defective adenovirus construct used is a serotype 5 adenovirus (Ad5) containing deletions in E1 (Ad5 base pairs 342-3523) and E3 (Ad5 base pairs 28133 to 30818). For adenovirus serotype 2 (Ad2), the E1 deletions are preferably bps 559-3503 and the E3 deletions are preferably bps 28812-29773. (Genbank gb:J01917). Those of skill in the art can easily determine the equivalent sequences for other serotypes, such as serotypes 4, 12, 6, 17, 24, 33, 42, 31, 16.

In one example of the invention, adenoviral serotypes 2 and 5, particularly 5, may be used. since at this point in time, more is known about these serotypes generally than other serotypes, and their complete DNA sequences are known. The prototype serotype 5 adenovirus has been completely sequenced (Chroboczek et al, 1992 J. Virology 186:280). They also belong to the subgroup C adenoviruses, which are not associated with human or rodent malignancies. However, it is envisioned that any adenovirus serotype can be used in this invention, including non-human ones, as deletion of E1 genes should render all adenoviruses non-tumorogenic. Also it may be advantageous to use a serotype which has less prevalence in the wild, as patients are less likely to have previous exposure (and less pre-existing antibodies) to a rarer serotype.

The recombinant adenoviruses according to the present invention can be prepared by any technique known to those of ordinary skill in the art (Levrero et al., Gene 101 (1991) 195, EP 185 573; Graham, EMBO J. 3 (1984) 2917). In particular, they can be prepared by homologous recombination between an adenovirus and a plasmid carrying, inter alia, the F protein-encoding DNA sequence. The homologous recombination occurs after co-transfection of the said adenoviruses and plasmid into an appropriate cell line. The cell line used should preferably (i) be transformable by the said elements and (ii) contain the sequences capable of complementing the defective adenovirus genome part, preferably in integrated form in order to avoid risks of recombination. As an example of a cell line, there may be mentioned the human embryonic kidney line 293 (Graham et al., J. Gen. Virol. 36 (1977) 59) which contains especially, integrated into its genome, the left-hand part of the genome of an Ad5 adenovirus (12%).

The vaccine composition of the present invention may further comprise one or more adjuvants. The term "adjuvant" as used herein refers to an agent that enhances the immunogenicity of an antigen but is not necessarily immunogenic. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

In the other aspect, the present invention provides a method of preventing RSV infection or RSV infection-related diseases comprising administering to a subject in need thereof a vaccine composition comprising a replication-defective recombinant adenoviral construct carrying a nucleotide sequence encoding a polypeptide of the F protein of RSV or fragments thereof.

RSV infection-related diseases include, but not limited to, otitis media, bronchilitis, eosinophilia, and pneumonia.

As demonstrated in the examples below, the vaccine composition of the present invention effectively elicits mucosal immune response when administered intranasally. Therefore, although the vaccine composition of the present invention may be administered via any traditional route such as subcutaneous, intradermal, intramuscular and intravenous injection, it is preferably administered transmucosally via, for example, the nasal or oral (intragastric) routes. In a preferred embodiment of the present invention, the vaccine composition is administered intranasally.

Other modes of administration including suppositories and oral formulations may also be desirable. Any suitable formulations for vaccines may be formulated by incorporating into the vaccine composition of the present invention pharmaceutically acceptable excipients, such as water, saline, glycerol, and ethanol, and substances such as wetting agents, emulsifying agents, or pH buffering agents.

The vaccine composition of the present invention may also be co-administered with antigens from other pathogens as a multivalent vaccine.

The present invention will now be described more specifically with reference to the following embodiments, which are provided for the purpose of demonstration rather than limitation.

Example 1

Expression of RSV F Antigen by rAd5-F Constructs

Construction and Production of rAd-F0 and rAd-F0ΔTM

Human embryonic kidney cells (293A) [Invitrogen, CA, USA] were grown and maintained in DMEM medium (Hyclone, Cat No. SH300) supplemented with 10% fetal bovine serum (Biological), and 1% penicillin/streptomycin (Biological) in an incubator maintained at 37° C. and equilibrated with 5% $CO_2$. RSV-B1 fusion (F) glycoprotein genes encoding the full length of F protein, F0 (SEQ ID NO: 1) and F0ΔTM (SEQ ID NO: 3, lacking the sequence coding for the transmembrane domain) were individually amplified by PCR and inserted into the shuttle vector, pENTRY4 (Invitrogen), to facilitate the subsequent recombination of inserted F gene into the ΔE1/ΔE3 (replication-incompetent) Ad5 vector, pAd/CMV/V5-DEST (Mizuguchi and Kay, Efficient construction of a recombinant adenovirus construct by an improved in vitro ligation method. Hum Gene; Ther 1998 Nov. 20; 9(17):2577-83; and Mizuguchi and Kay, A simple method for constructing E1- and E1/E4-deleted recombinant adenoviral vectors; Hum Gene Ther 1999 Aug. 10; 10(12):2013-7). The Recombinant plasmids pAd-F0, and pAd-F0ΔTM DNA were individually transfected into the packaging cell line, 293A, to produce the respective recombinant adenoviruses, designated as rAd-F0 and rAd-F0ΔTM, respectively (FIG. 1A).

Purification and concentration of the recombinant constructs were achieved by ultracentrifugation through a 15% sucrose/PBS gradient at 20,000 rpm for 60 min. The viruses were then resuspended in PBS, pH 7.2, and their titers determined by the modified standard plaque assay described. Briefly, varying dilutions of rAd-F0ΔTM rAd-F0 viruses were added to 293A cells plated in each well of a 6-well tissue culture plate. After overlaying the cultures with DMEM containing 0.75% methylcellulose, the cultures were incubated at 37° C. for 10 to 12 days and plaques were counted. The yield of rAd-F0 and rAd-F0ΔTM was usually around $1 \times 10^9$ pfu/mL.

Determination of RSV F Gene Expression in rAd-F0- and rAd-F0ΔTM-Infected 293A Cells Protocol described for live RSV infection of 293A cells was used to determine the infectivity of rAd-F0 or rAd-F0ΔTM and assess the expression of their respective F genes. To this end, $2 \times 10^6$ 293A cells were infected with $2 \times 10^5$ pfu of either rAd-F0 or rAd-F0ΔTM. Three days later, cells were collected by scraping and placed into a 50.0 mL sterile centrifuge tube (Corning). Harvested cells were divided into equal parts, and were washed twice, each time with 10.0 mL of ice-cold PBS, pH 7.2 to remove residual FBS. Total RNA was extracted from one part of the cell pellet using RNeasy Mini kit (Qiagen) according to the protocol provided by the supplier. cDNA was then generated using the SuperScript Reverse™ II reverse transcriptase kit (Invitrogen). The forward and reverse primers: 5'-ACATCGACAAGCAGCTGCTGC-3' (forward; SEQ ID NO: 5) and 5'-GAGGTGAAC-CTGTGCAACG-3' (reverse; SEQ ID NO: 6) were used to amplify and detect the 593-1151 region of the full length of F1 mRNA transcribed from the F0 (of 1722 nucleotides, SEQ ID NO: 1) and F0ΔTM (of 1572 nucleotides, SEQ ID NO: 3) inserts. The molecular size of the PCR product obtained was expected to be 559 bps. The fragment covering the nucleotide sequence 13-390 was amplified by using the F2 primer pairs: 5'-ATCCTGAAGGCTAAGGCTATC-3' (forward; SEQ ID NO: 7), and 5'-ACCAACGTGACCCTGTCCAA-3' (reverse; SEQ ID NO: 8) to generate a PCR product was expected to be 378 bps. Using primers specific to β-actin as Internal control in the RT-PCR was included (Invitrogen, CA, USA). The PCR products were analyzed by agarose electronpheresis.

The PCR products were analyzed by agarose electrophoresis. The second cell pellet was lysed to release the intracellular proteins for immunoblot analysis. Cell lysis was performed by treating the cell pellet with a pH 8.0 lysis buffer (containing 50 mM Tris-HCl, 150 mM NaCl, 1% Triton X-100, and 1× protease inhibitor cocktail (Roche). Lysis was allowed to take place on ice for 30 minutes with occasional pipetting. Cell debris was removed by centrifugation at 14,000×g for 20 minutes at 4° C. The cell lysate was subjected to SDS-PAGE electrophoresis, and proteins were transferred onto a Hybond ECL nitrocellular membrane (Amersham). The membrane was blocked with 5% skim milk in Tris-buffer saline, pH 7.2, at room temperature for 1 hour, washed twice with PBS containing 0.05% Tween 20 (PBST) and incubated with a polyclonal human antiserum raised against RSV (a gift from Burney S. Graham, NIH, USA) at 4° C. overnight. The membrane was washed twice with PBST, and an anti-human horseradish peroxidase (HRP)-conjugated antibody (KPL Immunochemical) diluted at 1 in 5000 in PBS containing 5% skim milk was then added to the membrane for protein visualization. Alternatively, 1:500 diluted polyclonal sera from recombinant adenoviruses-immunized mice were used to be primary antibody to blot HIRSV-B1-transferred membrane. After washing, a 1:20000 diluted HRP-conjugated donkey anti-mouse polyclonal serum as secondary antibody was used (Jackson). After 1 hour incubation at room temperature, the membrane was washed twice with PBST before it was treated with SuperSignal West Pico chemiluminescent substrate (Pierce), and exposed onto an X-ray film.

Upon transfection into competent 293A cells which constitutively expressed the E1 protein, the recombinant adenoviruses were shown to express their respective F inserts, as judged by RT-PCR reaction. The result showed that the PCR products corresponding to 378 bps and 559 bps were obtained via amplification of the 13-390 and 593-1151 nucleotide region of RSV F0 (F2+F1) or RSV F0ΔTM (F2+F1ΔTM) cDNA with the F2 and F1 primer pairs, respectively, from 293A cells transfected with rAd-F0 or rAd-F0ΔTM (FIG. 1B). In contrast, mRNA fragments of these sizes were not generated by 293A cells infected with the control construct, rAd-LacZ. Translated products of the F0 and F0ΔTM mRNAs were identified to have the molecular sizes of 62 KDa and 57 KDa, respectively, as judged by immunoblot analysis using a polyclonal murine antiserum raised against live RSV (FIG. 1C).

Example 2

RSV-Specific Humoral Responses Generated in Mice Immunized with rAd-F0 and rAd-F0ΔTM Constructs Preparation of RSV-B1, -Long and -A2 Strain Stocks Human larynx carcinoma cells (Hep-2) provided by Dr. Burney Graham of National Institute of Health, USA were grown and maintained in DMEM medium (Hyclone, Cat No. SH300) supplemented with 10% fetal bovine serum (Biological), and 1% penicillin/streptomycin (Biological) in an incubator maintained at 37° C. and equilibrated with 5% $CO_2$.

The human RSV-B1 (VR-1580), -long (VR-26) and -A2 (VR-1540) strains (purchased from the American Type Culture Collection) were propagated in Hep-2 cells. Hep-2 cells were grown in 150 mm Petri dish (Corning) up to 80% confluency before they were inoculated at an m.o.i. (multiplicity of infection) of 0.2 of RSV-B1, -long or -A2 isolates. Infection was allowed to take place for 4 days before the infected cells were harvested by scraping. Virus-containing Hep-2 cells were collected into a sterile 50.0 mL centrifuge tube (Beckman), and pelleted by centrifugation for 5 min at 3000 rpm. The cell pellet was disrupted using a tissue grinder to release the virions. Cell debris were removed by centrifugation at 3,000 rpm for 10 min. Partial purification of the individual viruses was performed by centrifugation of cell supernatants through a 15% sucrose (in PBS) gradient for 2 hours at 30,000 rpm. The virus was collected and resuspended in PBS, pH 7.2. The titer of RSV was determined by a standard plaque assay. Briefly, 100.0 μL of varying dilutions of purified virus preparations were added to $5\times10^5$ Hep-2 cells cultured in a 12-well plate (Corning). Each of the cultures was then overlaid with DMEM containing 1.5% methylcellulose (Sigma-Aldrich) and incubated for 5 to 6 days for the plaques to develop. Cells were stained with hematoxylin and eosin plaques were counted under a light microscope. The concentration of the individual virus is expressed as plaque-forming units per mL (pfu/mL).

Immunization and Live RSV Challenge of Mice

Six to eight week-old female BALB/c mice were purchased from the National Laboratory Animal Center, Taiwan. Mice were maintained in pathogen-free cages at the Animal Care Center of National Health Research Institutes throughout the animal study.

The four groups of BALB/c mice were anesthetized with isoflurane and primed with $1\times10^7$ pfu/50 μL of rAd-F0ΔTM, rAd-F0, rAd-LacZ and heat-inactivated RSV (HIRSV-B1) via the intranasal (i.n.) route. Twenty (20) days later, animals were boosted at an interval of 20 days apart either i.n., subcutaneously (s.c.), or intraperitoneally (i.p.) with the same dose of the respective immunogens. Mice were bled 14 days after priming or 10 days after booster immunization, serum samples were individually analyzed against HIRSV-B1 or Ad5 in ELISA, and virus-specific neutralizing activity. For challenge studies, $1\times10^6$ pfu of live RSV-B1 was administered intranasally thirty days after the second immunization.

Individual BALB/c mice ($H-2^d$) was intranasally administered with $1\times10^7$ pfu rAd-F0, rAd-F0ΔTM or, rAd-LacZ as control. Animals of a separate group were give the same pfu equivalent of HIRSV-B1 via the same immunization route to evaluate the virus-specific immune responses elicited as compared to those by the recombinant adenoviruses. The results of the ELISA assays obtained from two independent experiments are summarized in Table 1.

TABLE 1

ELISA of immune serum collected from different experimental groups of mice

| | Post-priming | | | | Post-boost | | | | | |
|---|---|---|---|---|---|---|---|---|---|---|
| | Exp 1 | | Exp 2 | | Exp 1 | | | Exp 2 | | |
| | | | | | Anti-RSV-B1 titer* | | | Anti-RSV-B1 titer* | | |
| Immunogen | Anti-RSV-B1 titer* | Anti-Ad5 titer** | Anti-RSV-B1 titer* | Anti-Ad5 titer** | i.n. | s.c. | i.p. | i.n. | s.c. | i.p. |
| rAd-LacZ | 0, 0, 0, 0, 0 (0) | 40, 80, 40, 10, 40 (42) | 0, 0, 0, 0, 0 (0) | 150, 160, 20, 40, 80 (92) | 0, 0, 0 (0) | 0, 0, 0 (0) | 0, 0, 0 (0) | 0, 0, 0 (0) | 0, 0, 0 (0) | 0, 0, 0 (0) |
| rAd-F0 | 0, 40, 80, 20, 80 (44) | 40, 20, 40, 40, 160 (60) | 10, 40, 20, 40, 60 (98) | 80, 40, 180, 180, 40 (96) | 2560, 1280, 2560, 5120, 640 (2432) | 5120, 5120, 10340, 5120, 2560, 10240, 1280 (8400) | 160, 2560, 5120, 2560, 10240 (4128) | 5120, 1260, 1280, 2560, 1280 (2904) | 5120, 2560, 5120, 1280, 2590 (3928) | 5120, 2560, 5120, 1280, 1280 (9072) |
| rAd-F0ΔTM | 80, 160, 80, 160, 40 (104) | 40, 40, 80, 80, 20 (52) | 80, 160, 40, 80 (88) | 160, 80, 40, 20, 80 (78) | 5120, 10240, 2560, 10240, 6120 (8858) | 10240, 20480, 5120, 10240, 5120 (10240) | 40060, 10240, 163840, 15980, 15980 (40152) | 2580, 5120, 2580, 5120, 2580 (3584) | 5120, 10240, 5120, 5120, 10240 (7158) | 10240, 20480, 10240, 5120, 20480 (13312) |
| HIRSV-B1 | 40, 160, 320, 80, 80 (138) | 0, 0, 0, 0, 0 (0) | 80, 80, 160, 160, 80 (112) | 0, 0, 0, 0, 0 (0) | 2580, 5120, 5120, 2580, 2580 (4808) | 2580, 10040, 5120, 10240, 2580 | 1280, 5120, 10240, 5120, 10240 (6400) | 2550, 2560, 2560, 5120, 1280 (2818) | 5120, 1 0240, 10240, 20480, 5120 (10240) | 10040, 20480, 5120, 20480, 5120 (12288) |

Five BALB/c mice in each experimental group were primed with $10^7$ pfu of rAd-F0, rAd-F0ΔTM, zAd-LacZ, or HIRSV-B1 via the i.n. route. The animals were boosted 20 days later with the same dose of the respective immunogens via either the i.n., s.c., or i.p. route. 14 days after priming, and 10 days after the booster immunization, serum samples from the experimental animals were collected and assayed against HIRSV-B1* and Ad5** (rAd-LacZ) in ELISA as described in M & M.
Anti-HIRSV-B1* and anti-Ad5** antibody titers showed were for individual mice with mean of the 5 animals in brackets in each experimental group of two studies performed independently.

It was found that serum samples collected from mice post intranasally primed with rAd-F0ΔTM and rAd-F0 gave mean HIRSV-B1-specific titers corresponding to 104 and 44, and, 88 and 38, respectively, in the two studies. The mean titer of the serum antibodies measured against immobilized HIRSV-B1 in the HIRSV-B1 immunized animals was 136 in experiment 1, and 112 in experiment 2. In contrast, no HIRSV-B1 reactivity was detected in the serum samples of mice primed with the empty vector, rAd-LacZ. rAd-LacZ component of the recombinant adenoviruses was immunogenic as evident from the low anti-rAd-LacZ (Ad5) IgG titers (mean) corresponding to 52 and 60 of mice intranasally administered once with rAd-F0ΔTM and rAd-F0, respectively; and 42 for animals administered with rAd-LacZ. In the second experiment, mean anti-AdS-specific titers measured in the immune sera of animals were 76 for rAd-F0ΔTM, 96 for rAd-F0 and, 92 for rAd-LacZ that was administered. Following booster immunization with the respective immunogen via intranasal, subcutaneous (s.c) or intraperitoneal (i.p.) route, HIRSV-B1 reactive titers assayed in the serum samples of the experimental groups of mice were found to be substantially increased. In experiment 1, the IgG antibody titers were in the range of 2560 and 5120 (mean=4608) for the animals administered i.n. twice with HIRSV-B1; and 2560 and 10240 (mean=6144), and 1280 and 10240 (mean=6400) for mice primed intranasally and boosted s.c. and i.p. with HIRSV-B1, respectively. In experiment 2, mean HIRSV-B1-binding antibody titers obtained from mice following booster inoculation with HIRSV-B1 were: 2816 via i.n., 10240 via s.c. and 12288 via i.p. routes. In both studies, serum anti-RSV-B1-specific IgG antibodies were not detected in mice given $1 \times 10^7$ pfu of rAd-LacZ under the three immunization routes tested. However, high titers of HIRSV-B1 IgG binding antibodies in the range of 2560 and 10240 (mean=6656), and, 2560 and 5120 (mean=3584) were detected in the sera of animals immunized intranasally with the same dose of rAd-F0ΔTM in experiments 1 and 2, respectively. These antibody levels were not markedly different from those detected in animals inoculated intranasally, followed by boosting either s.c. or i.p. with rAd-F0ΔTM. Compared to rAd-F0ΔTM, rAd-F0 was found to be slightly less immunogenic under the three immunization protocols tested. Serum HIRSV-B1-specific antibody titers were between 640 and 5120 (mean=2432), and 1280 and 5120 (mean=2304) in animals vaccinated intranasally with rAdF0 in experiments 1 and 2. For mice in experiment 1 that were primed intranasally and boosted either s.c. or i.p. with rAd-F0, HIRSV-B1 binding IgG antibody titers were within the range of 1280 and 10240 (mean=6400), and 160 and 10240 (mean=4128), respectively. Comparable HIRSV-B1-binding titers were detected in the immune sera of animals in experiment 2 boosted with rAd-F0 via the two immunization routes. Given the fact that rAd-LacZ immunization did not lead to the production of anti-HIRSV-B1 antibody responses, the specificity of the IgG antibodies in the immune sera of rAd-F0ΔTM and rAd-F0 vaccinated animals either after priming or booster immunization would be directed against the viral F protein. However, there is no difference of F-specific antibody responses in the three different administrative routes after statistical analysis. As intranasal vaccination is effective, we chose this route of immunization to further investigate the nature of the humoral as well as cellular responses elicited by rAd-F0ΔTM, and the less immunogenic rAd-F0 construct.

Determination of Serum and Bronchoalveolar Lavage (BAL) IgA and IgG Levels

Virus-specific IgG and IgA antibodies in immune sera and bronchoalveolar lavages (BALs) of the individual animals were determined by ELISA using HIRSV-B1 as target antigen. BAL fluids were collected by performing 2 consecutive washes of the airspace of the lungs of individual experimental mice, each time with 1.0 mL of sterile PBS containing 1× protease inhibitor coattail (Roche), pH 7.4. The samples obtained were stored in a −80° C. freezer until tested for their contents of RSV-specific IgA and IgG antibodies.

For ELISA, blood samples collected by tail vein puncture of the individual experiments mice 14 days after intranasal priming, and 10 days after the booster immunization were clotted at room temperature, then centrifuged at 12,000 rpm for 20 min. Sera were pipetted out and inactivated at 56° C. for 30 min. ELISA for the detection of RSV-specific IgG and IgA antibodies entailed coating wells of a 96-well Immulon 2B plate (Corning Life Sciences, USA) with $2.5 \times 10$ pfu of cesium chloride gradient-purified, heat-inactivated (75° C. for 1 hr) RSV-B1 virus in 100 uL of sterile sodium carbonate buffer (8.4 g/L NaHCO$_3$, and 3.5 g/L Na$_2$CO$_3$, pH 9.5) at 37° C. overnight. The Sera of the individual mice collected from tail sample bleeds on day 14 following intranasal priming with rAdF0ΔTM, rAd-F0 or, the empty vector, rAd-LacZ, were also assayed against rAd-LacZ immobilized on ELISA wells ($2.5 \times 10^4$ pfu of the virus per well) using the same coating condition to determine their contents of anti-adenovirus antibodies. All the antigen-coated ELISA wells were then blocked with 5% skim milk in PBS at room temperature for 1 hour and washed three times with 200 µL of PBS containing 0.05% Tween 20. Individual sera were 2-times serially diluted (80 to 163840) and 100 uL were added to virus-coated well for 2 hours at room temperature, and the reaction was allowed to take place at room temperature for 2 hours. Wells were washed three times with 200 µL of wash buffer (PBS containing 0.5% Tween 20). One hundred µL of either horseradish peroxidase (HRP)-conjugated donkey anti-mouse IgG antibodies (Jackson), or anti-mouse IgA antibodies (ZYMED) were then added to detect the binding of anti-RSV binding antibodies. After another one-hour incubation at room temperature, the plates were washed four times with the wash buffer, and 70.0 µL of SureBlue™ TMB peroxidase substrate solution (Kirkegaard & Perry Laboratories) were added to the wells. Following 15 min incubation in the dark, absorbance at wavelength 450 nm was recorded in an ELISA reader (SPECTRA NAX M2, Molecular Devices).

The same ELISA protocol was also used to determine IgA levels in the BALs.

Figure 2:
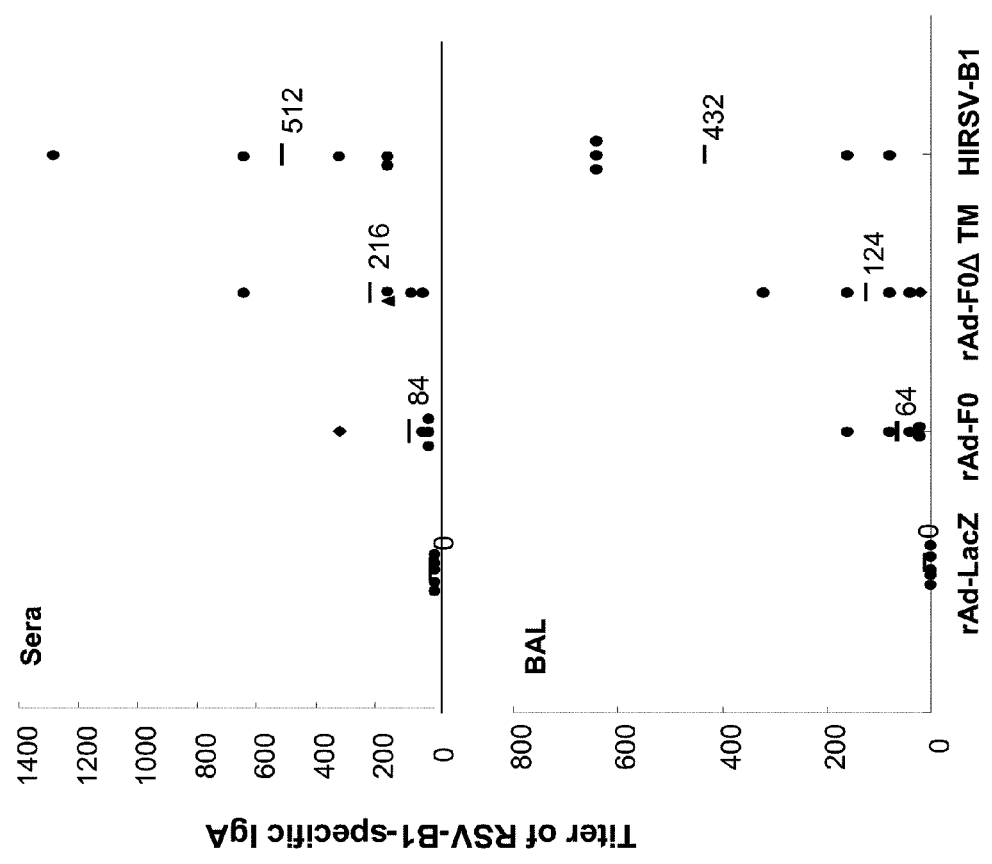

The results were summarized below. Mice primed intranasally (i.n.) with $1 \times 10^7$ pfu of the recombinant adenoviruses of the invention, or HIRSV-B1 and boosted either i.n., subcutaneously (s.c) or intraperitoneally (i.p.) with the priming dose of immunogen were found to mount comparable levels of anti-viral antibody responses. The IgG antibody titers measured against immobilized HIRSV-B1 were in the range of 2560 and 5120 (mean=4608) for the animals administered i.n. twice with HIRSV-B1, and 2560 and 10240 (mean=6144), and 1280 and 10240 (mean=6400) for mice primed intranasally and boosted s.c. and i.p. with HIRSV-B1, respectively. Serum anti-RSV-B1-specific IgG antibodies were not detected in mice given $1 \times 10^7$ pfu of rAd-lacZ under the three immunization routes tested. However, high titers of HIRSV-B1 IgG binding antibodies in the range of 2560 and 10240 (mean=6656) were detected in the sera of animals immunized intranasally with the same dose of rAd-F0ΔTM. These antibody levels were comparable to those detected in animals inoculated intranasally, followed by boosting either s.c. or i.p. with rAd-F0ΔTM. Compared to rAd-F0ΔTM, rAd-F0 was found to be less immunogenic regardless of the immunization schedule. Serum HIRSV-B1-specific antibody titers were between 640 and 5120 (mean=2432) in animals vaccinated intranasally with rAd-F0. For mice primed intranasally and boosted either s.c. or i.p. with rAd-F0, HIRSV-B1 binding IgG antibody titers were within the range of 1280 and 10240 (mean=6400), and 160 and 10240 (mean=4128), respectively (FIG. 2). Given the fact that rAd-lacZ immunization did not lead to the production of anti-HIRSV-B1 antibody responses, the specificity of the IgG antibodies in the immune sera of rAd-F0ΔTM and rAd-F0 vaccinated animals would be directed against the viral F protein. However, there was no difference of F-specific antibody responses in the three different administrative routes after statistical analysis. As intranasal vaccination was effective, the intranasal route was chosen for immunization to further investigate the nature of the humoral as well as cellular responses elicited by rAd-F0ΔTM, and the less immunogenic rAd-F0 construct.

Intranasal administration with either rAd-F0ΔTM or rAd-F0 also led to the production of F protein-specific IgA antibodies. IgA antibody titers in sera and BALs of mice immunized with rAd-F0ΔTM were found to be slightly lower than those in the samples from animals given HIRSV-B1, but significantly higher than the levels measured in the samples from mice vaccinated with rAd-F0 (FIG. 2). F protein-specific IgG antibodies were not detectable in the all BAL samples assayed (data not shown).

Example 3

Cross-Reactivity and Virus-Neutralizing Activity of Immune Sera Raised Against rAd-F0 and rAd-F0ΔTM Via the Intranasal Route Anti-RSV-B1 antibodies generated by the mice immunized via the intranasal route with rAd-F0ΔTM and rAd-F0 also cross-reacted with RSV-long and -A2 strains. The serum samples were collected from individual BABL/c mice administered twice with $10^7$ pfu of rAd-F0, rAd-F0ΔTM, rAd-LacZ, or HIRSV-B1, 10 days after the booster administration, and the titles were assayed against the heat-inactivated RSV-B1 (B1 strain pf RSV), RSV-long (Long strain of RSV) and RSV-A2 (A2 strain of RSV) immobilized on ELISA plate wells. As shown in the results in FIG. 3A, virus binding titers in sera from rAd-F0ΔTM-immunized mice were in the range of 5120 and 40960 (mean=18432) against the RSV-long strain, and 320 and 5120 (mean=1600) against the RSV-A2 strain. Immune sera raised against the less immunogenic rAd-F0 construct similarly showed moderate virus cross-reactivities. Mean RSV-long and RSV-A2 binding titers were 3968 and 1072, respectively, that were significantly lower than those obtained by rAd-F0ΔTM-immunization, but comparable to those obtained with rAd-F0. We further examined by immunoblotting whether the sera collected from rAd-F0ΔTM and rAd-F0 immunized mice were able to specifically recognize the F protein of RSV-B1 particles. The human polyclonal anti-RSV F antibody which binds to F1 subunit of RSV F protein, as well as sera from mice immunized with rAd-F0ΔTM and rAd-F0 but not rAd-LacZ also recognized the F protein (FIG. 3B). In blotted membrane, degraded F protein was also detected by sera from mice immunized with rAd-F0ΔTM and rAd-F0, respectively. This could be due to the preparation process of HIRSV-B1 particles.

Virus Neutralization Assay and Viral Load Determination

The RSV-specific neutralizing activity of immune sera was determined by mixing 50 μL of serially diluted sera (reconstituted with pre-immunized normal mouse sera to equal amount of sera) with 50.0 μL ($10^3$ pfu) of live RSV-B1, -long, or -A2 and incubated for 1 hour at 37° C. The mixture was then added to $2\times10^5$ Hep-2 cells in a 6-well plate. One hour later, wells were overlaid with a 1.5% (w/v) semi-solid methylcellulose. Hep-2 cell cultures treated with the same dose of virus were used as positive control. RSV induced syncytia-formation was assessed by light microscopy 5 days later, and syncytia reduction was calculated by regression analysis to obtain a 60% syncytia reduction titer (giving 60% inhibition of plaque-formation). A second similar set of experimental cultures were fixed with 3.7% formaldehyde and stained with 1% hematoxylin and eosin to develop plaques that were counted under a light microscope.

As shown in FIG. 4A, the sera from mice immunized with the recombinant adenoviruses were found to possess virus neutralizing activity. Higher RSV-B1-specific neutralizing titers were measured in mice immunized with rAd-F0ΔTM as compared to animals administered with rAd-F0. RSV-B1-specific neutralizing antibody levels in mice given HIRSV-B1 was within the range of 80 and 320 (mean=160), that was significantly higher than those generated in animals administered with the recombinant adenoviruses (FIG. 4A). Antibodies produced in mice immunized with the recombinant adenoviruses also exhibited potent cross-neutralizing activities against RSV A strains. The potency of the cross-neutralizing activities was greater in immune sera raised against rAd-F0ΔTM as judged by the mean titers of 116 and 104 against RSV-long and RSV-A2, as compared to mean titers of 64 and 56 in sera of rAd-F0-immunized animals. RSV-B1-neutralizing antibodies produced in HIRSV-B1 vaccinated mice also cross-neutralized RSV-long and RSV-A2 isolates with potency comparable to those from animals administered with rAd-F0ΔTM.

IgA antibodies in BAL samples of mice immunized with the recombinant adenoviruses at varying dilutions, 4×, 8×, 16×, 32×, 64× and 128×, respectively, as scored after 4 days of culture. As shown in FIG. 4B, similar to the virus neutralizing activity, a 1:4 dilution for each BAL sample for assay, BAL samples collected from mice immunized with rAd-F0 and rAd-F0ΔTM were found to inhibit RSV-B1 infection of Hep-2 cells. Unpaired, two-tailed Student t test was performed to compare the results obtained from the different experimental groups of mice. Results are considered statistically significant when the p value is <0.05 (symbols * and ** were used to indicate p values <0.05 and <0.01, respectively). No significant difference in virus neutralizing activity was noted between BAL samples harvested from these groups of experimental animals which have comparable titers of RSV-B1 binding IgA antibodies. BAL samples from HIRSV-B1-immunized mice that have significantly higher titers of virus-specific IgA antibodies, had greater potency of virus neutralization activities.

Example 4

Induction of Virus-Specific $CD4^+$ T-Cell Responses in rAd-F0ΔTM and rAd-F0 Immunized Mice In this example, an investigation regarding the F protein-specific $CD4^+$ lymphocyte response profile elicited in mice immunized with the rAd-F0ΔTM and rAd-F0 was conducted because it was known that an immunological help provided by $CD4^+$ helper T cells from the Th1 and Th2 phenotypes regulated antigen-specific humoral and cytotoxic T-cells (CTLs) responses.

Splenocyte suspensions were prepared from the spleens of individual experimental mice. After cell sedimentation, 5.0 mL of ice-cold red blood cell (RBC) lysing buffer (Gibco) was added to cell pellets. RBC lysis was facilitated by continuous gentle pipetting for 1 min. Lysis was stopped by adding 5.0 mL of culture medium (CM: DMEM (Gibco) supplemented with 10.0% fetal bovine serum, and 100 μg/mL of penicillin/streptomycin mix). Lymphocytes were pelleted by centrifugation at 2,000 rpm for 5 min, and washed one more time with 10.0 mL of CM. Splenocytes ($2\times10^6$) were then cultured in a 24-well tissue culture plate (Corning) in the presence or absence of $10^3$ pfu of HI-RSB-B1. Cultures were kept in a 5.0% $CO_2$ incubator at 37° C. Culture supernatants were collected 48 hr later, and stored at −80° C. until tested. Th1 (IFN-γ) and Th2 (IL-4, IL-5, IL-10 and IL-13) cytokines as well as IL-17 present in culture supernatants were quantitated by using the respective antibody-pairs purchased from eBioseceince (IL-13-Cat. No. 88-7137-88; IL-17-Cat No 88-7371-88; IL-4-Cat. No. BMS609MST; IL-5-Cat. No. BMS610MST; IL-10-Cat. No. BMS614MST). Recombinant IFN-γ and IL-13 used as standards were from eBioscience and recombinant IL-4, IL-5 and IL-10 were purchased from Bender MedSystems, Inc.

Figure 5:
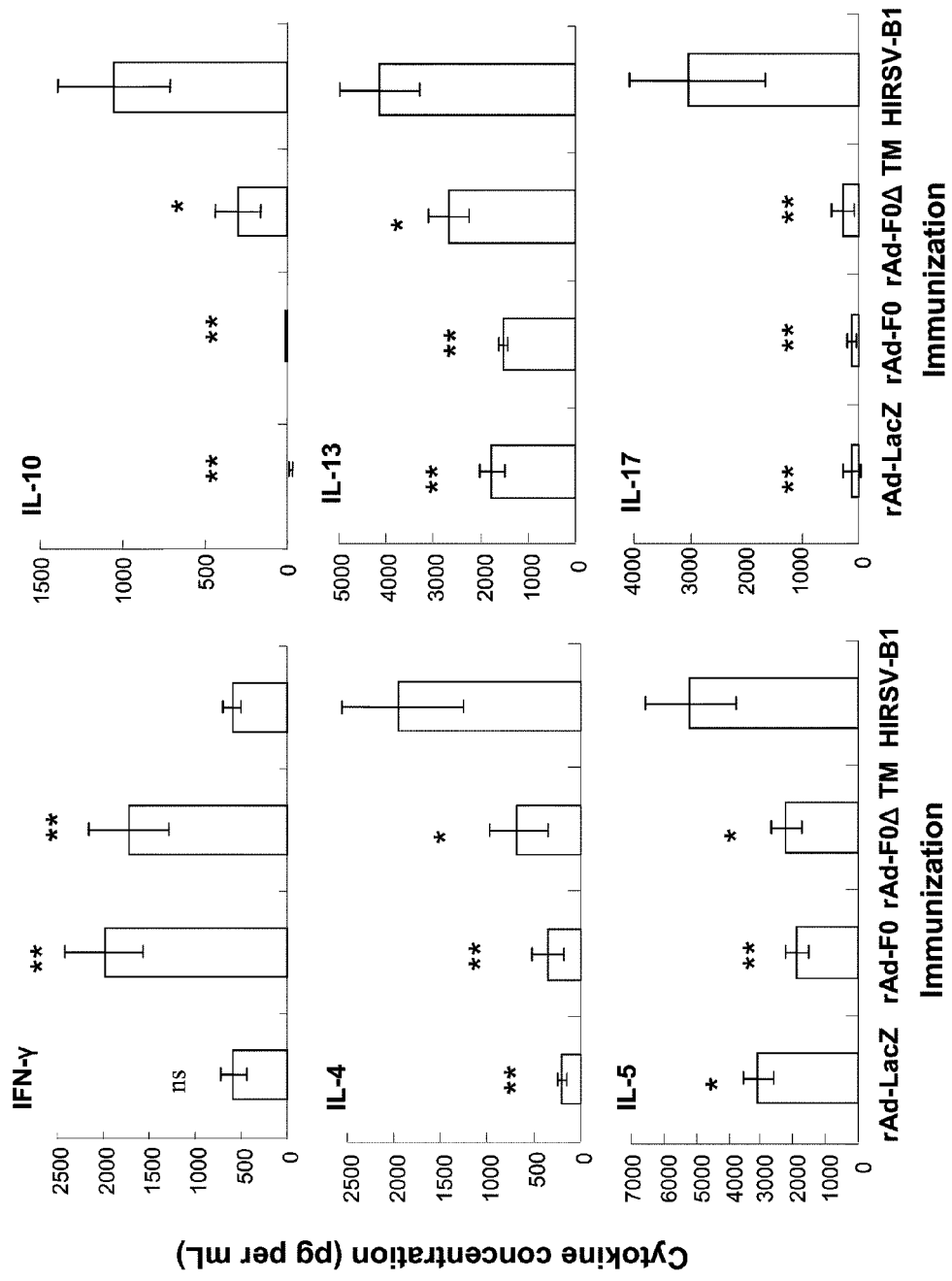
FIG. 5 shows the RSV-specific CD4+ T-cell responses elicited in the mice immunized twice via the intranasal route with rAd-LacZ, rAd-F0, rAd-F0ΔTM, or HIRSV-B, wherein the results were expressed as the concentrations of each cytokine in pg per mL (* and ** represented p<0.05 and p<0.01, respectively, and it was indicated that the responses were significantly different from that of the HIRSV-B1-immunized group; P>0.05 indicates the values were not significantly different).
Figure 6:
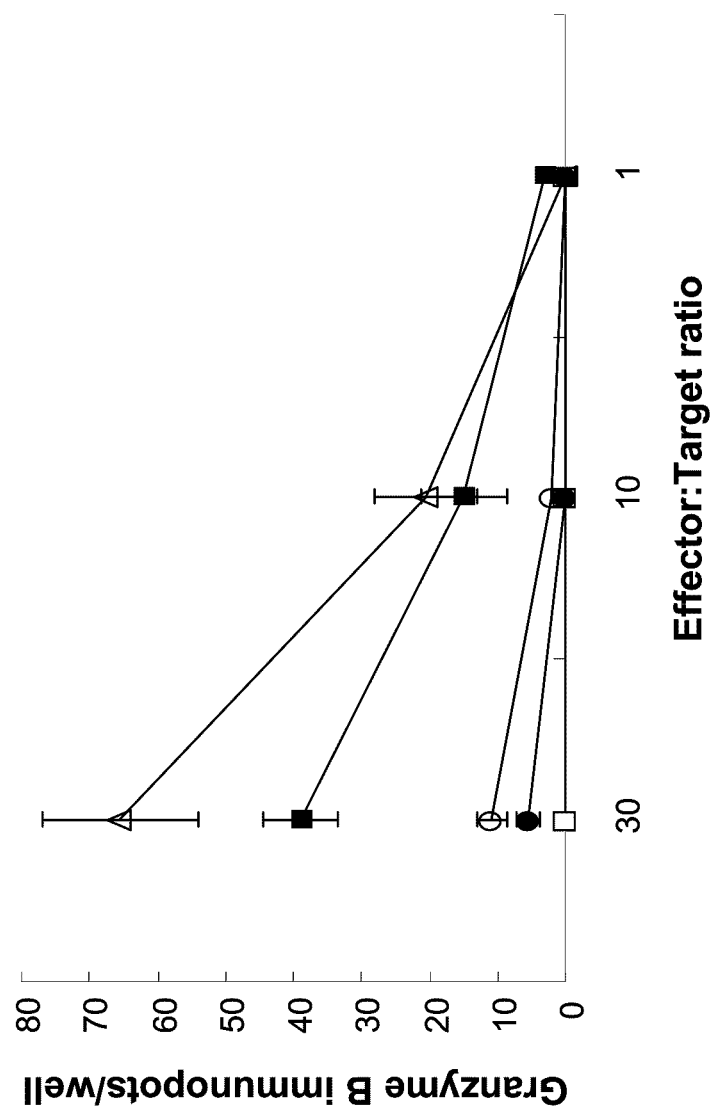
FIG. 6 shows the enumeration of granzyme B-secreting cells in the spleens of experimental mice; wherein the splenocytes prepared from mice immunized with rAd-LacZ (●), rAd-F0 (■), rAd-F0ΔTM (▲), HIRSV-B (○), or PBS buffer (□); wherein the results were expressed as number of granzyme B immunospots+/- two standard deviations for each experimental group.
Figure 7:
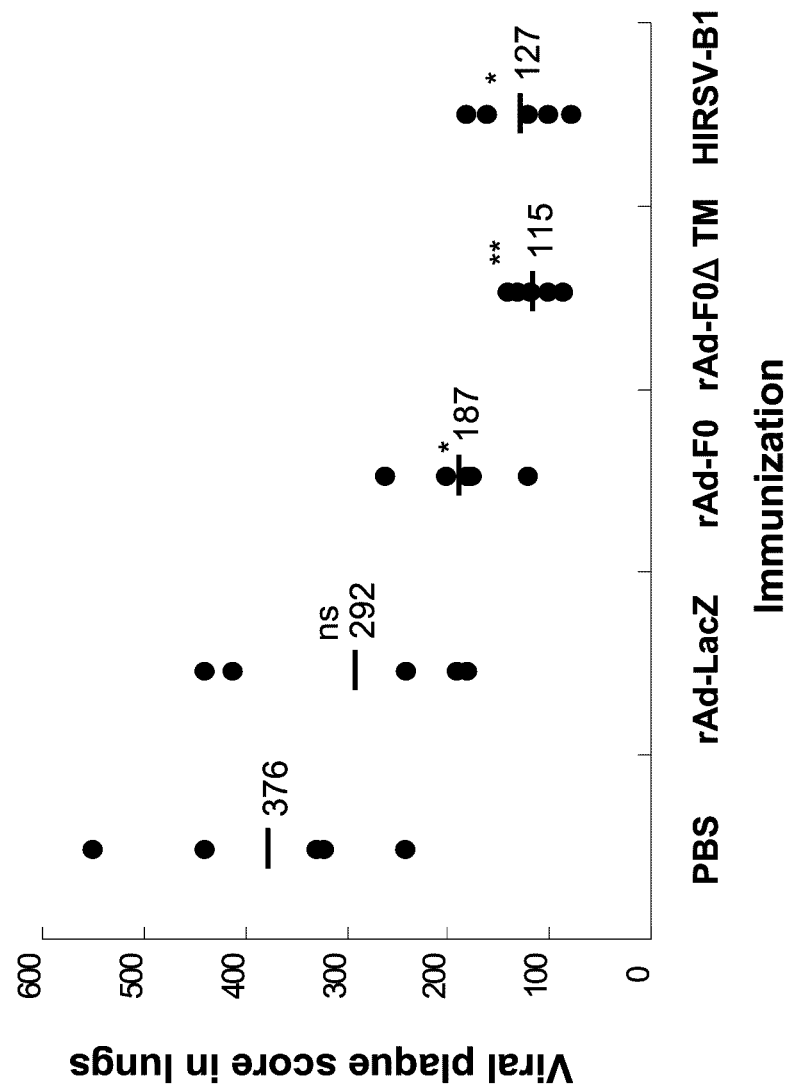
FIG. 7 shows the viral plaque determination in the lungs of experimental mice, wherein the results are expressed as plaque numbers for each experimental mouse (* and ** represented p<0.05 and p<0.01, respectively, and it was indicated that the results were significantly different from that of the PBS-immunized control).
Figure 9:
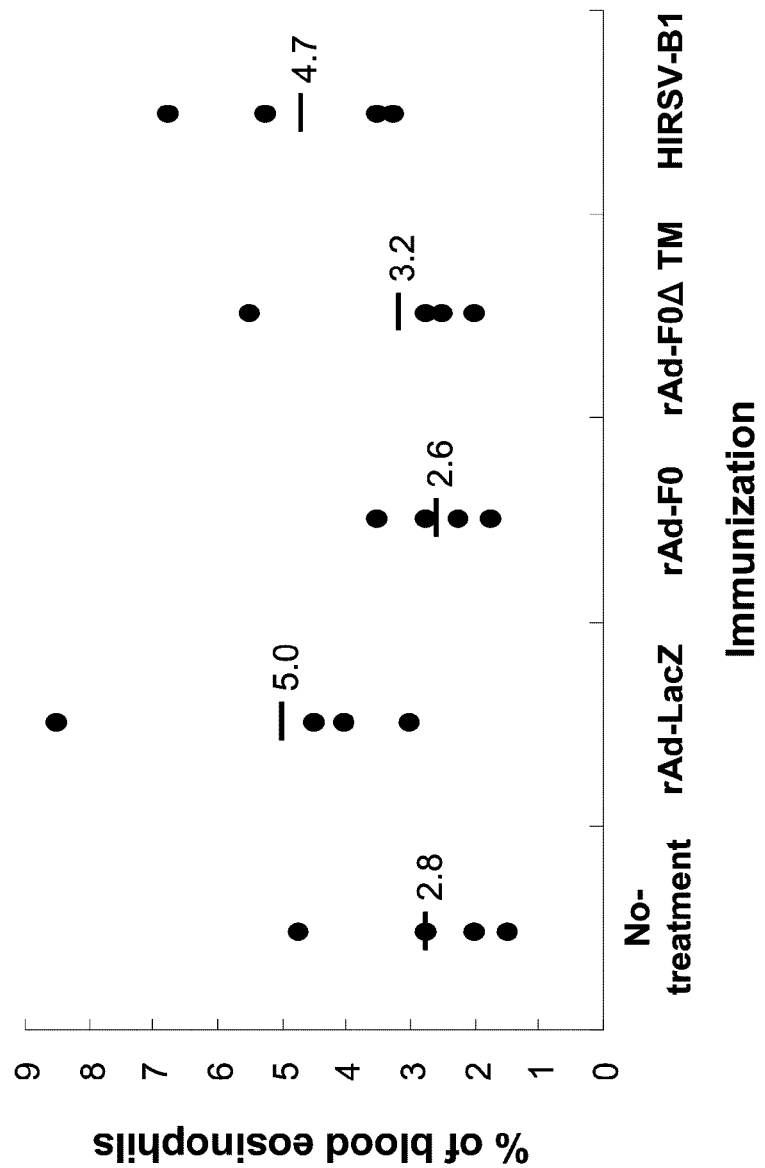
FIG. 9 shows the blood eosinophilia in the untreated and vaccinated mice; wherein the results were expressed as % eosinophils per total leucocytes.

Following in vitro restimulation with HIRSV-B1, lymphocytes of mice immunized with the control construct, rAd-LacZ, produced a background level of IFN-γ corresponding to 582±138 pg/mL (mean). In contrast, significantly higher IFN-γ levels of 1709±433 pg/mL and 1988±429 pg/mL were measured in the supernatants of HIRSV-B1-stimulated splenocyte cultures of mice administered with rAd-F0ΔTM and rAd-F0, respectively (FIG. 5). As shown in FIG. 5, the splenocytes from the HIRSV-B1 immunized group secreted lower amount of IFN-γ (593±100 pg/mL). Within the panel of Th2 cytokines assayed, IL-4 means of 663±322 and 349±168 pg/mL, IL-5 means of 2221±483 and 1855±375 pg/mL, IL-10 at mean of 300±138 pg/mL and non-detectable, and IL-13 means of 2669±426 and 1520±94 pg/mL were secreted by lymphocytes from rAd-F0ΔTM and rAd-F0 immunized mice, respectively, following stimulation with HIRSV-B1. In comparison, RSV-B1 stimulation of splenocytes of HIRSV-B1-vaccinated mice leaded to the production of significantly higher level of these cytokines Another notable observation is that splenocytes from HIRSV-B1-immunized mice produced a considerable amount of IL-17 (3042±1398 pg/mL) in response to HIRSV-B1 stimulation. This is in sharp contrast to the barely detectable amount of IL-17 secreted by splenocytes of animals immunized with rAd-F0ΔTM, or rAd-F0. Given the above, the significant secretion of IL-17 was not found HIRSV-B1-timulated spleen cells of rAd-LacZ vaccinated animals, the results indicated that RSV-B1 F protein driven activation of $CD4^+$ cells would not lead to the differentiation of a subpopulation that bear the IL-17 producing phenotype.

Example 5

Induction of RSV F-Specific CTLs in Ad-F0 and Ad-F0ΔTM-Vaccinated Mice

In this example, the effect on immunization with rAd-F0ΔTM and rAd-F0 constructs leading to the induction of F-specific CTLs was investigated in order to detect the apoptotic death of target infected cells. A granzyme B ELISPOT assay was used to measure the frequencies of CTLs directed against a $F_{85\text{-}93}$ peptide, KL-9 (KYKNAVTEL). KL-9 was known as a peptide containing an immunodominant H-$2K^d$-resticted epitope of the RSV F protein in the spleens of immune animals, and to comprise a dominant $K^d$-restricted CTL epitope from RSV F protein in the presence of 10 U/mL of recombinant IL-2 at 37° C. for 5 days (Chang J, Srikiatkhachorn A, Braciale T J. Visualization and characterization of respiratory syncytial virus F-specific CD8(+) T cells during experimental virus infection. J Immunol 2001 Oct. 15; 167(8):4254-60).

Granzyme B release ELISPOT assay previously described to determine the effector function of antigen-specific CTLs (Shafer-Weaver K, Sayers T, Strobl S, Derby E, Ulderich T, Baseler M, et al. The Granzyme B ELISPOT assay: an alternative to the 51Cr-release assay for monitoring cell-mediated cytotoxicity. J Transl Med 2003 Dec. 29; 1(1):14) was used to assess the presence of RSV F protein-specific CTLs in the spleens of the immunized animals. The assay entailed culturing $5\times10^6$ splenocytes with 2.0 μg per mL of a KL-9 peptide. Target cells (p815 cells) were supplemented with 2.0 μg per mL of a KL-9 peptide at a ratio of 30:1, 10:1, and 1:1 in anti-granzyme B capture antibody coated well for 2 days at 37° C. prior use in assay. Unpulsed p815 cells served as negative control. $10^4$ target cells per well (100 μL) were added to wells of a 96-well plate pre-coated with capture monoclonal antibodies (0.1 μg per well) (R&D) specific for murine granzyme B following the appropriate number of in vitro restimulated splenocytes culture (as effectors cells). The defined effector:target (E:T) ratios were plated in triplicate. Two days later, the cells were damped off and the plates were washed three times with wash buffer before adding 100 μL of PBS-Tween 20 containing 0.25 μg of the detection monoclonal antibody specific for mouse granzyme B. The plates were left at 4° C. for overnight, washed four times with wash buffer, 100 μL of streptavidin-alkaline phosphatase were added and the plates were incubated at room temperature for 2 hr. The wells were washed again four times before 100 μL of substrate (BCIP/NBT) were added to develop the immunospots. After 30 min incubation in the dark, the plates were washed with water, left to dry, and the number of immunospots was scored using the ELISPOT reader (C.T.L. IMMUNOSPOT, CELLULAR TECHNOLOGY LTD).

Following co-culturing of splenocytes (effector) from rAd-LacZ-immunized mice with $10^4$ P815 (target) cells loaded with the KL-9 peptide at effector/target ratios of 30:1, 10:1, and 1:1, a mean background number of granzyme B-secreting effector splenocytes cells was scored. In contrast, rAd-F0ΔTM immunized mice mounted a significantly more vigorous KL-9-restricted response than animals administered with rAd-F0. No KL-9-restricted CTL response was detected in mice immunized with HIRSV-B1 (FIG. 6).

Example 6

Immunoprotective Efficacy of Ad-F0ΔTM and Ad-F0 Constructs Against Live RSV Challenge The anti-viral humoral and cellular responses elicited via intranasal immunization with rAd-F0ΔTM and rAd-F0 were assessed in parallel to those generated by HIRSV-B1 vaccination for their immunprotective ability against live RSV challenge. The parameters selected to assess protection included measurement of viremia in the lungs, recovery from initial weight loss, and blood eosinophilia.

Lung Viral Load Determination

Mice were individually immunized via the intranasal route twice with relevant immunogens before they were intranasally challenged with $10^6$ pfu of live RSV-B1. Viral plaques in the lungs of individual mouse was determined 5 days after challenge using the plaque-forming assay. Whole lungs from individual experimental mice were removed, and homogenized. The homogenized tissues were centrifuged at 3,000 rpm for 10 min at 4° C. to sediment cell debris. Supernatants were collected, serially diluted, and tested for their ability to infect Hep-2 cells in the plaque formation assay. In FIG. 7, horizontal bars represented the means of plaques obtained for each experimental group.

As shown in FIG. 7, a marked reduction in lung viral plaque number (127±42) was observed in animals immunized with two doses of HIRSV-B1, and challenged with $1\times10^6$ pfu of live RSV-B1 virus, as compared to 376±120 plaques detected in the lungs of mice immunized with the control rAd-LacZ vector. A similar level of protection was observed in mice vaccinated with rAd-F0ΔTM, whereas animals immunized with rAd-F0 were slightly less protected (FIG. 7).

Body Weight Loss

Progressive body weight was determined for each of the mice challenged with live RSV-B1 regardless of whether they were immunized with rAd-F0ΔTM, rAd-F0, rAd-LacZ or HIRSV-B1, in addition to an untreated group in the study. Each animal was then intranasally inoculated with $10^6$ pfu of live RSV B1. The body weight of each mouse was recorded daily. The results in FIG. 8 showed the initial body weight loss occurred in mice following challenge with live RSV-B1 virus regardless of whether they were preimmunized with rAd-F0ΔTM, rAd-F0, rAd-LacZ or HIRSV-B1. The maximal body weight lost was found to reach in day 2 post virus challenge in experimental groups of mice pre-immunized with rAd-F0, rAd-F0ΔTM, or HIRSV-B1. In these experimental groups, progressive body weight recovery was then seen in these animals after this time. In contrast, body weight loss in PBS-administered and rAd-LacZ immunized mice went a day further and reached their maxima at day 4 before recovering occurred. By day 7, body weight was restarted back to normal in mice of each of the experimental groups.

Blood Eosinophilia Determination

The mice were individually immunized via the intranasal route twice with the immunogen before they were intranasally challenged with $10^6$ pfu of live RSV-B1. Peripheral blood samples obtained by tail vein puncture 7 days post-live RSV challenge were collected in sterile Eppendorf vial (Corning) containing 5.0 μL of 3% EDTA. Five μL of blood were smeared onto a glass slip. The blood sample was dried at room temperature, and then stained with 1.0-2.0 mL of Wright-Giemsa stain solution (Sigma-Aldrich) for 1.5 min at room temperature. Excess stain was washed by rinsing the glass slips twice with deionized water. After air-drying, eosinophils identified as red/pink cells were counted under an oil immersion microscope, and their numbers were scored as percentage of total leukocytes.

As shown in FIG. 9, the results of blood eosinophil counts showed that 2.6% and 3.2% of leukocytes were eosinophils in mice immunized with rAd-F0- and rAd-F0ΔTM, respectively (FIG. 9). However, these values were not statistically different from those found in unimmunized control animals. For the rAd-LacZ, and HIRSV-B1 preimmunized mice, blood eosinophilia was 5.0% and 4.7%, respectively, following live RSV-B1 challenge. These seemingly higher values, however, was not also statistically different from those obtained from unvaccinated animals, or mice vaccinated with rAd-F0, rAd-F0ΔTM, or rAd-LacZ.

The above examples showed that the F0 and F0ΔTM proteins expressed in mice vaccinated with the respective recombinant adenoviruses are immunogenic as judged by the induction of F protein-specific humoral and cellular immune responses. F protein-specific antibodies present in sera and BALs of mice primed and boosted with rAd-F0ΔTM and rAd-F0 using either i.n./i.n., i.n./s.c., or i.n./i.p. routes are virus neutralizing. It is further demonstrated that serum antibodies elicited by adenovirus constructs cross-react with the F proteins of the RSV-long and A2 strains. A notable finding in the present invention is the effectiveness of the intranasal delivery of the recombinant adenoviruses at inducing F-specific IgA antibodies in bronchoalveolar lavages of immune mice. Intranasal immunization with rAd-F0ΔTM and rAd-F0 also allowed for the correct processing of the RSV F protein to generate MHC class 1-restricted CTLs.

The anti-viral immunity elicited by rAd-F0 and rAd-F0ΔTM constructs confers protection against live RSV-B1 virus challenge. This is evident from the significantly lower viral load recovered from the lungs of animals immunized intranasally with the recombinant adenoviruses, but not with the rAd-LacZ control construct. Vaccination with rAd-F0 or rAd-F0ΔTM constructs allows for an accelerated recovery from initial body weight lost following live RSV challenge, faster than that observed in mice given rAd-LacZ. Protection studies showed that resistance to RSV challenge is greater in mice administered with rAd-F0ΔTM that mount stronger virus-neutralizing antibody and CTL responses than animals immunized with the less immunogenic rAd-F0 construct.

Since there is no current RSV vaccine available, a heat-inactivated RSV preparation is used in the present invention to compare the anti-viral humoral responses contributing to protection against RSV infection. Indeed, mice immunized with HIRSV-B1 produced virus-specific binding and neutralizing antibodies at significantly higher levels than those administered with either rAd-F0 or rAd-F0ΔTM, and were found to be at least equally protected from live RSV challenge. In summary, HIRSV-B1-immunized mice did not mount CTL responses, which anti-viral immunity could be attributed to neutralizing antibodies generated against the F protein, and the G antigen that also contained virus-neutralization epitopes. However, as observed in the vaccinated mice with the recombinant adenovirus construct of the invention followed by a live RSV post challenge, the level of eosinophilia was significantly lower than that in the mice pre-immunized with HIRSV-B1 followed by a live RSV post challenge. Accordingly, it was concluded that the immunization with HIRSV-B1, instead of the F protein-expressing adenovirus construct of the invention, leaded to the generation of T cells that secreted an enhanced level of Th2 cytokines It is also observed here that Splenocytes from mice immunized with HIRSV-B1, produced markedly higher level of IL-17 as compared to those from the mice vaccinated with the recombinant adenovirus construct of the invention, rAd-F0. Unexpectedly, Th17 cells producing IL-17 (associated with inflammation) were not detected in the spleens of the mice vaccinated with the vaccine of the invention, Ad-F0ΔTM. The above findings suggested that the presentation of the G glycoprotein, and the transmembrane portion of the F protein might drive the differential development of CD4+ cells to acquire the Th17 phenotype in addition to the Th1 and Th2 phenotypes. Because Th17 cells was found to be substantially associated with various aspects of inflammation (Annunziato et al, The phenotype of human Th17 cells and their precursors, the cytokines that mediate their differentiation and the role of Th17 cells in inflammation; Int Immunol 2008 November; 20(11):1361-8.), the recombinant adenovirus vaccines of the present invention utilizing the F protein of RSV (in place of the glycoprotein) could avoid such undesired side effect, inflammation, while maintaining great immunizing effect.

All publications and patent documents cited in this application are incorporated by reference in their entirety for all purposes to the same extent as if each individual publication or patent document were so individually denoted.

We claim:

1. A vaccine composition for reducing respiratory syncytial virus (RSV) infection comprising a replication-defective recombinant adenoviral construct in which the E1 and E3 genes are deleted or inactive, the construct expressing a RSV protein and containing the nucleotide sequence of SEQ ID NO: 1 or SEQ ID NO: 3 as the only sequence encoding the RSV protein, wherein the vaccine composition induces protective immunity against RSV infection in the absence of an undesired inflammatory responses or eosinophilia.

2. The vaccine composition of claim 1, wherein the construct contains the nucleotide sequence of SEQ ID NO: 1 as the only sequence encoding the RSV protein.

3. The vaccine composition of claim 1, wherein the construct contains the nucleotide sequence of SEQ ID NO: 3 as the only sequence encoding the RSV protein.

4. The vaccine composition of claim 1, wherein the construct is a serotype 5 adenovirus (Ad5) construct.

5. The vaccine composition of claim 1, which is administered transmucosally.

6. The vaccine composition of claim 1, which is administered intranasally.

7. A method of reducing respiratory syncytial virus (RSV) infection comprising administering to a subject in need thereof a vaccine composition comprising a replication-defective recombinant adenoviral construct in which the E1 and E3 genes are deleted or inactive, the construct expressing a RSV protein and containing the nucleotide sequence of SEQ ID NO: 1 or SEQ ID NO: 3 as the only sequence encoding the RSV protein, wherein the vaccine composition is administered in an amount effective for inducing an immune response against RSV infection in the absence of an undesired inflammatory responses or eosinophilia.

8. The method of claim 7, wherein the construct contains the nucleotide sequence of SEQ ID NO: 1 as the only sequence encoding the RSV protein.

9. The method of claim 7, wherein the construct contains the nucleotide sequence of SEQ ID NO: 3 as the only sequence encoding the RSV protein.

10. The method of claim 7, wherein the construct is a serotype 5 adenovirus (Ad5) construct.

11. The method of claim 7, wherein the vaccine composition is administered transmucosally.

12. The method of claim 7, wherein the vaccine composition is administered intranasally.

13. The vaccine composition of claim 1, wherein the undesired inflammatory response is associated with an increase of interleukin (IL)-17.

14. The vaccine composition of claim 1, wherein the eosinophilia is associated with an increase of T cell type 2 (Th2)-associated cytokines selected from the group consisting of IL-4, IL-5, IL-10 and IL-13.

15. The method of claim 7, wherein the undesired inflammatory responses is associated with an increase of IL-17.

16. The method of claim 7, wherein the eosinophilia is associated with an increase of Th2-associated cytokines selected from the group consisting of IL-4, IL-5, IL-10 and IL-13.

* * * * *